(12) United States Patent
Ng et al.

(10) Patent No.: US 11,284,804 B2
(45) Date of Patent: Mar. 29, 2022

(54) WEARABLE NON-INVASIVE APPARATUS FOR AND METHOD OF ENHANCING LOWER LIMBS VENOUS RETURN OF A SUBJECT

(71) Applicant: Agency for Science, Technology and Research, Singapore (SG)

(72) Inventors: Xu Wen Ng, Singapore (SG); Wan Loong James Mok, Singapore (SG); Enci Mary Kan, Singapore (SG); Ka Mung Chee, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 773 days.

(21) Appl. No.: 15/781,014

(22) PCT Filed: Nov. 24, 2016

(86) PCT No.: PCT/SG2016/050580
§ 371 (c)(1),
(2) Date: Jun. 1, 2018

(87) PCT Pub. No.: WO2017/095330
PCT Pub. Date: Jun. 8, 2017

(65) Prior Publication Data
US 2020/0298004 A1  Sep. 24, 2020

(30) Foreign Application Priority Data
Dec. 1, 2015 (SG) ............................. 10201509867X

(51) Int. Cl.
*A61N 1/36* (2006.01)
*A61B 5/02* (2006.01)
(Continued)

(52) U.S. Cl.
CPC ........ *A61B 5/02007* (2013.01); *A61B 5/4836* (2013.01); *A61N 1/0452* (2013.01);
(Continued)

(58) Field of Classification Search
USPC .......................................................... 607/48
See application file for complete search history.

(56) References Cited

U.S. PATENT DOCUMENTS 6,282,448 B1   8/2001 Katz et al.
2011/0178572 A1   7/2011 Czyrny et al.
(Continued)

FOREIGN PATENT DOCUMENTS

FR   2869808 A1   11/2005
WO   03090845 A2   11/2003
(Continued)

OTHER PUBLICATIONS

Breen et al., "Comparison of Single- and Two-Channel Neuromuscular Electrical Stimulation Sites for Enhancing Venous Return," IEEE Transactions on Neural Systems and Rehabilitation Engineering, vol. 20, No. 3, May 2012, pp. 389-394.
(Continued)

*Primary Examiner* — Nicole F Lavert
(74) *Attorney, Agent, or Firm* — Shackelford, Bowen, McKinley & Norton, LLP

(57) ABSTRACT

In various embodiments, a wearable non-invasive apparatus for enhancing lower limb venous return of a subject may be provided. The apparatus may include a monitoring device configured to determine a venous state of a subject such as a photoplethysmography (PPG) sensor. The apparatus may also include a neuromuscular electrical stimulation (NMES) device configured to generate an electrical stimulus in response to the determined venous state and concurrently stimulate the triceps surae and the deep posterior calf muscle
(Continued)

of the subject with the generated electrical stimulus to enhance lower limb venous return. In an alternative embodiment, electrical stimulation can be at the tibial nerve of the subject to retrograde target the triceps surae and the deep posterior calf muscle of the subject.

15 Claims, 19 Drawing Sheets

(51) Int. Cl.
*A61B 5/00* (2006.01)
*A61N 1/04* (2006.01)
*A61B 5/024* (2006.01)
*A61B 5/11* (2006.01)
*A61B 5/145* (2006.01)

(52) U.S. Cl.
CPC ......... *A61N 1/0484* (2013.01); *A61N 1/0492* (2013.01); *A61N 1/36003* (2013.01); *A61N 1/36031* (2017.08); *A61B 5/02416* (2013.01); *A61B 5/112* (2013.01); *A61B 5/1116* (2013.01); *A61B 5/1118* (2013.01); *A61B 5/14542* (2013.01); *A61B 5/4824* (2013.01); *A61N 1/36034* (2017.08)

(56) References Cited

U.S. PATENT DOCUMENTS

| | | | | |
|---|---|---|---|---|
| 2011/0313482 A1* | 12/2011 | Dupelle | ............... | A61H 31/004 607/3 |
| 2013/0281815 A1* | 10/2013 | Varadan | ................. | A61B 5/282 600/388 |
| 2014/0257016 A1* | 9/2014 | Ahmed | .............. | A61N 1/36034 600/9 |
| 2014/0303460 A1* | 10/2014 | Corley | ................. | A61B 5/0205 600/301 |

FOREIGN PATENT DOCUMENTS

| | | |
|---|---|---|
| WO | 2006054118 A1 | 5/2006 |
| WO | 2010070332 A1 | 6/2010 |
| WO | 2013069002 A1 | 5/2013 |
| WO | 2016128985 A1 | 8/2016 |

OTHER PUBLICATIONS

Written Opinion of the International Searching Authority for International Application No. PCT/SG2016/050580 dated Feb. 26, 2017, pp. 1-8.

International Preliminary Report of Patentability issued by the International Bureau of WIPO for International Application No. PCT/SG2016/050580 dated Jun. 5, 2018, pp. 1-9.

* cited by examiner

Identifying the head of the fibula on the superiolateral aspect of the calf — 402

Extend a leg with the foot placed at maximal active or passive dorsiflexion — 404

Identify the soleus to run between the posterior edge of the fibula and the anteriolateral aspect of the gastrocnemius muscle along the superior third of the calf — 406

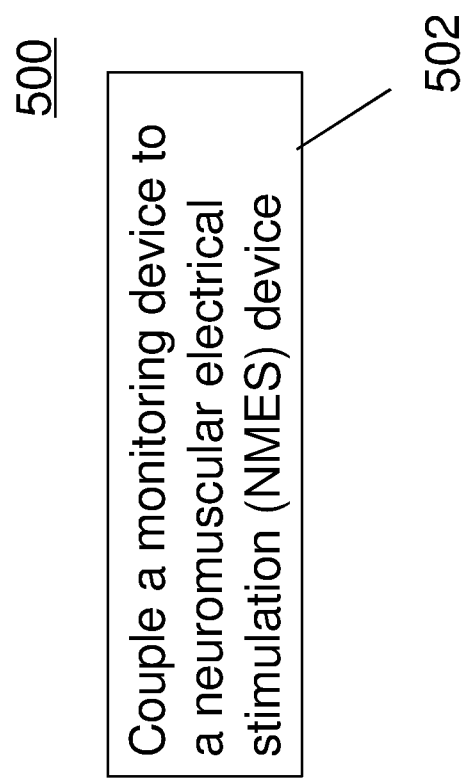

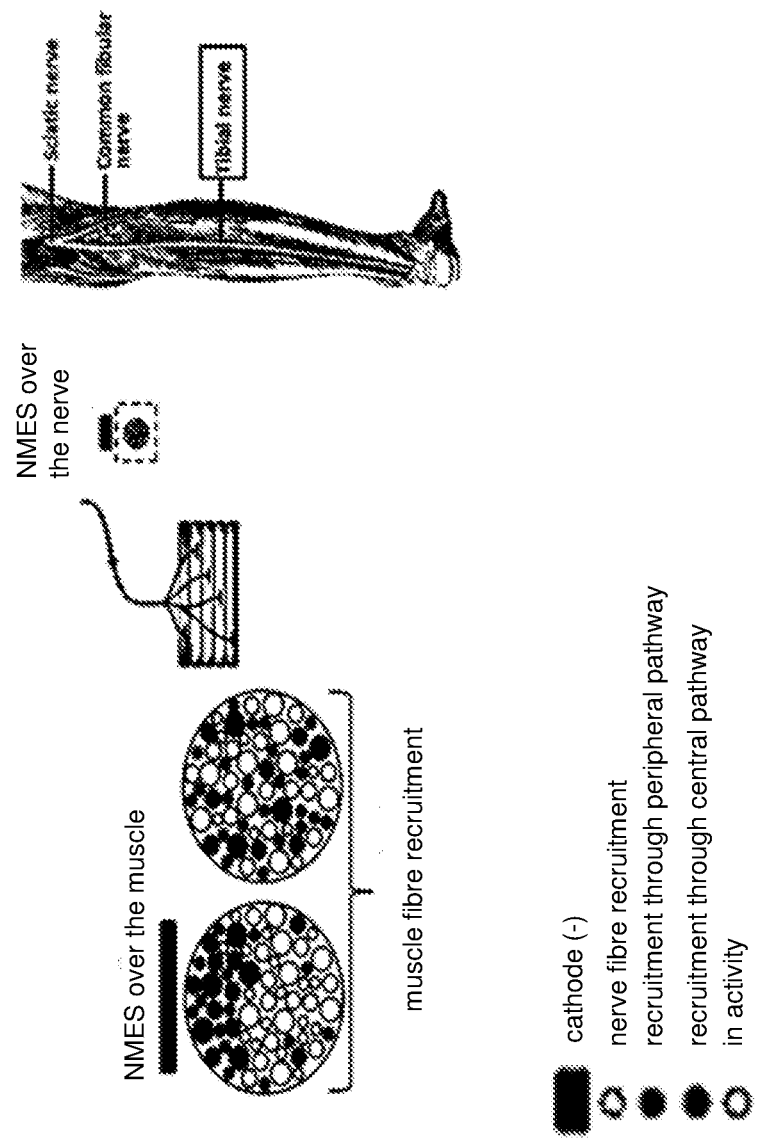

FIG. 7D
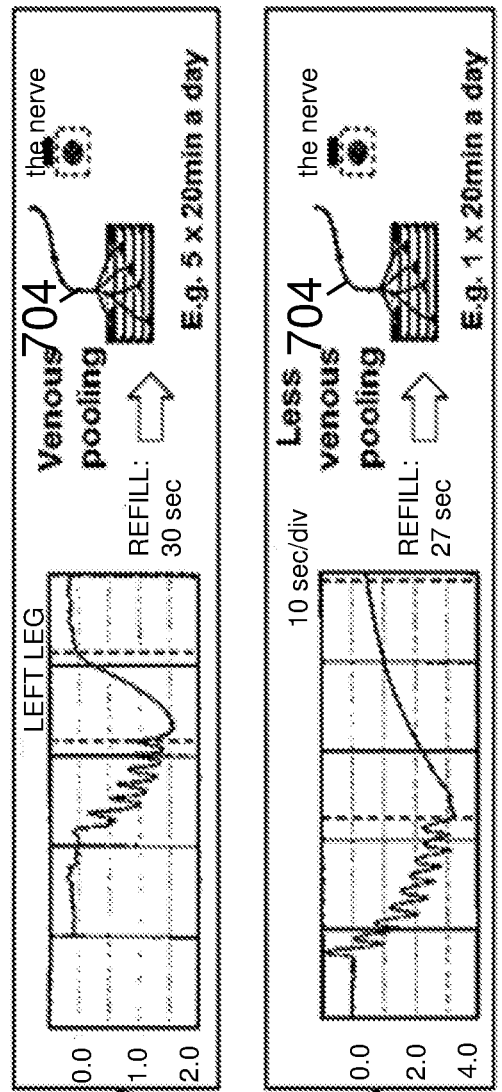
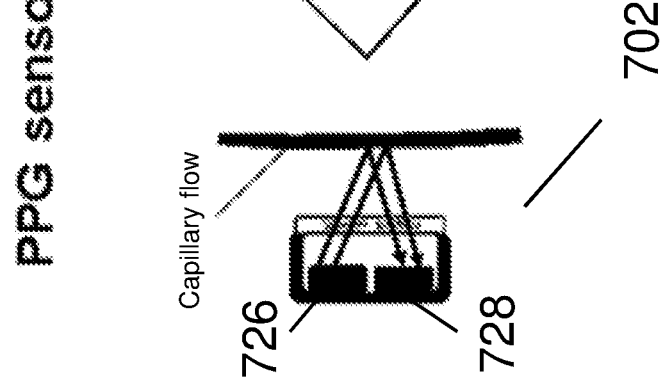

Posterior tibial nerve stimulation gave a significant increase in mean peak venous velocity and flow volume at the popliteal vein compared to baseline resting venous return

WEARABLE NON-INVASIVE APPARATUS FOR AND METHOD OF ENHANCING LOWER LIMBS VENOUS RETURN OF A SUBJECT

CROSS-REFERENCE TO RELATED APPLICATION

This application claims the benefit of priority of Singapore application No. 10201509867X filed Dec. 1, 2015, the contents of it being hereby incorporated by reference in its entirety for all purposes.

TECHNICAL FIELD

Various aspects of this disclosure relate to wearable non-invasive apparatuses for enhancing lower limbs venous return of subjects. Various aspects of this disclosure relate to methods of enhancing lower limbs venous return of subjects.

BACKGROUND

Chronic venous insufficiency (CVI) of lower limbs is one of the most widespread diseases occurring in developed countries worldwide, with varicose veins affecting more than 25 million adults in the United States, and with than 6 million people suffering from more advanced venous diseases. The male to female prevalence ratio is about 1.5 to 3.5. CVI is the cause of ulcerations in 60% to 80% of patients with chronic leg ulcers. Venous leg ulcers (also called stasis or varicose ulcers) are extremely common in the United States and affect between 500,000 to 2 million people annually. It has been reported in literature that 53% of patients with venous ulcers have reflux in the superficial system alone, 32-44% of patients have reflux in both superficial and deep venous systems, and 5-15% of patients have reflux in the deep venous system alone. Currently, superficial reflux is adequately addressed via superficial vein ablation, but treatment options for deep vein reflux remain few and far between. Current maintenance/symptomatic treatments for all patients with advanced CVI involve use of compression garments which have universal poor compliance.

One of the contributing factors for venous return in the lower extremities is venous pumping mechanisms at or near the feet. Approximately 90% of the venous return in the lower extremities is through the deep veins through the action of the foot, calf, and thigh muscle pumps. Among the three pumps, the calf pump has the largest capacitance, generates the highest pressures, and is of the greatest importance. The ejection fraction of the calf muscle pump is 65%, in comparison with only 15% for the thigh pump. The calf muscle pump is the primary force enhancing return of venous blood from the lower extremity to the heart. It causes displacement of venous blood in both vertical and horizontal directions, generates ambulatory pressure gradient between thigh and lower leg veins, and bidirectional streaming within calf perforators. It has been observed that the function of the calf muscle pump is impaired in patients with chronic venous disease. The incidence of ulceration increases with decreasing values of calf muscle pump ejection fraction. In CVI patients, their calf muscle pump function is often impaired and they have limited range of motion which affects the extent of plantar- and dorsi-flexion that engages the calf muscle pump during ambulation.

SUMMARY

In various embodiments, a wearable non-invasive apparatus for enhancing lower limb venous return of a subject may be provided. The apparatus may include a monitoring device configured to determine a venous state of a subject. The apparatus may also include a neuromuscular electrical stimulation (NMES) device configured to generate an electrical stimulus in response to the determined venous state and concurrently stimulate the triceps surae and the deep posterior calf muscle of the subject with the generated electrical stimulus to enhance lower limb venous return.

In various embodiments, a method of enhancing lower limb venous return of a subject may be provided. The method may include determining a venous state of a subject. The method may also include generating an electrical stimulus in response to the determined venous state. The method may further include concurrently stimulating the triceps surae and the deep posterior calf muscle of the subject with the generated electrical stimulus.

BRIEF DESCRIPTION OF THE DRAWINGS

The invention will be better understood with reference to the detailed description when considered in conjunction with the non-limiting examples and the accompanying drawings, in which:

FIG. 4 is a schematic showing a method of accurately identifying skin based access to targeted calf muscles, deep posterior muscles, or a nerve that targets the calf muscles according to various embodiments.

FIG. 5 is a schematic showing a method of forming a wearable non-invasive apparatus for enhancing lower limb venous return of a subject according to various embodiments.

FIG. 7C is a schematic showing the targeting of the posterior tibial nerve to stimulate superficial and deep muscles via peripheral and central pathways according to various embodiments.

FIG. 7D is a schematic illustrating the use of a monitoring device according to various embodiments including a photoplethysmography (PPG) sensor as an indicator of venous pooling.

DETAILED DESCRIPTION

Figure 1:
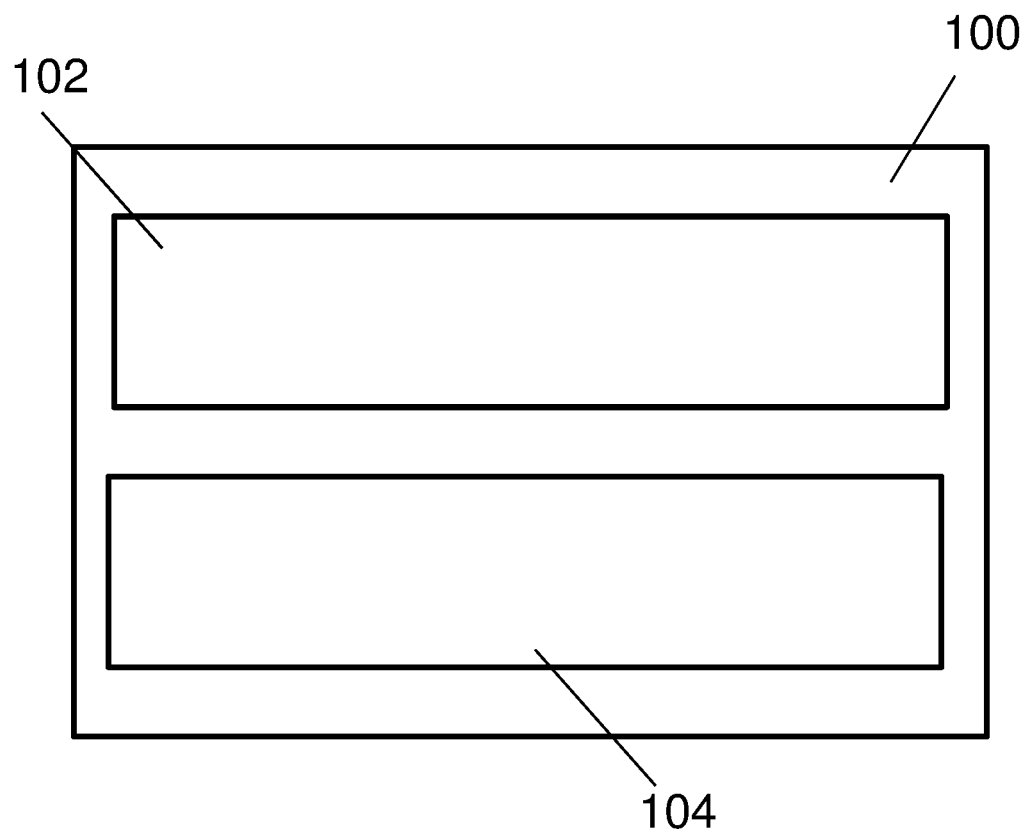
FIG. 1 shows a schematic of a wearable non-invasive apparatus for enhancing lower limb venous return of a subject according to various embodiments.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Embodiments described in the context of one of the methods or devices are analogously valid for the other methods or devices. Similarly, embodiments described in the context of a method are analogously valid for a device, and vice versa.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

In the context of various embodiments, the articles "a", "an" and "the" as used with regard to a feature or element include a reference to one or more of the features or elements.

In the context of various embodiments, a first layer over a second layer may refer to the first layer on the second layer, or may refer to the first layer separated from the second layer by one or more intervening layers.

In the context of various embodiments, the term "about" or "approximately" as applied to a numeric value encompasses the exact value and a reasonable variance.

As used herein, the term "and/or" includes any and all combinations of one or more of the associated listed items.

Various embodiments seek to alleviate or address the abovementioned issues. Various embodiments provide an apparatus that seeks to increase venous return in the lower limbs of a human body or an animal body.

Various embodiments concurrently stimulate the triceps surae and the deep posterior calf muscle to achieve a synergistic effect in increasing venous return in the lower limbs. This may be made possible by identifying the nerve that innervates all of these muscles, which is the tibial vein. The tibial vein is deeply located at the popliteal fossa which may require a large amount of electrical current to effect stimulation. Various embodiments may seek to stimulate the targeted muscles via retrograde targeting through the posterior tibial nerve, a branch of the tibial nerve. However, various other embodiments may target other parts of the tibial nerve that is upstream or downstream of the posterior tibial nerve, or may target another nerve, or may directly target one or more muscles of interest.

FIG. 1 shows a schematic of a wearable non-invasive apparatus 100 for enhancing lower limb venous return of a subject according to various embodiments. The apparatus 100 may include a monitoring device 102 configured to determine a venous state of a subject. The apparatus 100 may also include a neuromuscular electrical stimulation (NMES) device 104 configured to generate an electrical stimulus in response to the determined venous state and concurrently stimulate the triceps surae and the deep posterior calf muscle of the subject with the generated electrical stimulus to enhance lower limb venous return.

In other words, the apparatus 100 may include an electrical stimulation device 104 which provides electrical stimulation to the muscles of a subject, as well as a monitoring device 102 which monitors the venous state of a venous system or a blood circulation system of the subject.

Various embodiments may provide a wearable non-invasive apparatus for enhancing lower limb venous return of a subject, wherein the apparatus may be arranged to be placed in contact with a skin surface around an ankle of the subject. Various embodiments may provide a selective neuromuscular electrical stimulation (NMES) device 104 for deep calf muscle activation to enhance lower limb venous return. In various embodiments, the monitoring device 102 may be meant to provide a dynamic feedback for informing the NMES device 104.

In the current context, a non-invasive apparatus may refer to an apparatus which does not penetrate into the body of the subject. The term "subject" as used herein may generally refer to a person, but may also refer to an animal, such as a monkey or a gorilla. In various embodiments, the subject may refer to an user of the apparatus and/or a patient.

In various embodiments, the monitoring device 102 may be a first component of the apparatus 100, while the electrical stimulation device 104 may be a second component of the apparatus 100.

The apparatus 100 may further include at least one electrode adapted to be positioned at or within a predetermined distance from the triceps surae of the subject, or the deep posterior calf muscle of the subject, or a tibial nerve of the subject to retrograde target the triceps surae and/or the deep posterior calf muscle of the subject. As non-limiting examples, the at least one electrode may be positioned within 10 cm, or within 5 cm, or within 2 cm or within 1 cm, from the triceps surae of the subject, or the deep posterior calf muscle of the subject, or the tibial nerve of the subject. The NMES device 104 may be configured to provide retrograde neurostimulation of a posterior tibial nerve of the subject.

The at least one electrode may be electrically coupled or may be coupleable to the NMES device 104. The electrical stimulus generated by the NMES device 104 may be applied to the triceps surae of the subject, and/or the deep posterior calf muscle of the subject, and/or the tibial nerve of the subject via the at least one electrode. The application of the electrical stimulus to a muscle, e.g. the triceps surae and/or the deep posterior calf muscle, may cause the muscle to contract for promoting movement of venous blood from the limbs to the body. The application of the electrical stimulus to the tibial nerve of the subject may stimulate the triceps surae and/or the deep posterior calf muscle of the subject, and may indirectly cause the triceps surae and/or the deep posterior calf muscle for promoting movement of venous blood from the limbs to the body.

The triceps surae is a pair of muscles located at the calf, and consists of the two-headed gastrocnemius muscle and the soleus muscle. The at least one electrode may be adapted or may be configured to be positioned at or within a predetermined distance from the triceps surae selected from the group consisting of the gastrocnemius muscle and the soleus muscle. In the context of various embodiments, the gastrocnemius muscle is where the two muscle bellies meet or along the inferior midline before the two muscle bellies diverge. In the context of various embodiments, the soleus muscle may be accessed via the superior third of the posterior calf, in between the medial and lateral heads of the gastrocnemius, or accessed via the inferiolateral aspect of the posterior calf or via the superiolateral aspect of the calf.

The at least one electrode may be adapted or configured to be positioned at or within a predetermined distance from the deep posterior calf muscle selected from the group consisting of a flexor digitorum longus muscle, flexor hallucis longus, posterior tibialis and popliteus muscles. In the context of various embodiments, the flexor digitorum longus muscle is the lateral side of the tibia at the junction between the upper ⅓ and middle-third of the lower limb. In the context of various embodiments, the flexor hallucis longus muscle is situated on the fibular side of the leg and arises from the inferior two-thirds of the posterior surface of the body of the fibula, with the exception of 2.5 cm at its lowest part. In the context of various embodiments, the posterior tibialis muscle is at the posterior groove of the tibia above the medial malleolus. In the context of various embodiments, the popliteus muscle is a small muscle located at the knee joint.

Additionally or alternatively, the at least one electrode may be adapted or configured to be positioned at or within a predetermined distance from the tibial nerve through a posterior tibial nerve. In the context of various embodiments, the tibial nerve is deep within the popliteal fossa at the back of the knee. In the context of various embodiments, the posterior tibial nerve is a posterior edge of the medial malleolus. The posterior tibial nerve is downstream of the tibial nerve, peroneal nerve and popliteal nerve. The specific area of stimulation may be the posterior tibial nerve which may be superficially stimulated from behind the ankle medial malleolus of the subject. Using the apparatus 100 in accordance with various embodiments, stimulation at the posterior tibial nerve as opposed to the tibial nerve behind the popliteal fossa may require significantly less electrical current and may be able to elicit efficacy at electrical parameters that may be tolerable and comfortable, allowing the apparatus to be used whilst ambulatory.

In various embodiments, the at least one electrode may not penetrate into the body of the subject.

The apparatus 100 in accordance with various embodiments may harness both the calf muscle pump and venous foot pump of the subject. For example, the apparatus in accordance with various embodiments may harness the foot muscles by stimulating the deep posterior calf muscles i.e. posterior tibialis, flexor hallucis longus, flexor digitorum longus and popliteus muscle which are involved in foot plantar flexion to activate the venous foot pump indirectly to achieve the desired effect.

The apparatus 100 in accordance with various embodiments may target the superior/superficial and deep muscles of the subject.

Identification of the deep muscles may not be apparent either from knowledge of the anatomy (medical professionals) or through MRI scans. The apparatus in accordance with various embodiments may be used with amputated legs to identify regions for optimal access as the targeted access areas. The targeting of the superficial and deep posterior calf muscles via the posterior tibial vein may be through a retrograde and/or afferent pathway. This may be apparent as literature (on existing devices and methods) has targeted the main tibial nerve, popliteal nerve and peroneal nerve.

The at least one electrode may be or may be part of a disposable pad configured to be placed in contact with a skin surface around an ankle of the subject or at least substantially near to an ankle of the subject. In various embodiments, the at least one electrode may form an integral part of the disposable pad (or may be referred to as an electropad). In various embodiments, the at least one electrode may be electrically coupled or may be coupleable to the disposable pad. For example, the disposable pad may include a disposable adhesive pad.

In various embodiments, the at least one electrode may be electrically coupled or may be coupleable to the monitoring device 102.

The venous state may include at least one of an outflow fraction, a venous filling index, a venous refill time (VRT), an ejection volume, an ejection fraction, a venous volume, and a residual volume fraction. The venous state may be determined via at least one of plethysmography (PPG), skin turgor, edema, tissue oxygen perfusion, pain, inflammation, and induration.

Photoplethysmography (PPG) may be used as a measure of venous stasis to enhance the delivery of the stimulation. This may be used in conjunction with breathing state to further enhance the delivery of the stimulation. Assessments of the breathing cycle, for example, inspiration-expiration, may also be incorporated to harness the use of the intra-abdominal pressure on top of the calf muscle and venous foot pump to stimulate venous return.

There are many reported ways for which the degree of chronic venous insufficiency (CVI) may be estimated via, for example, venous pressure, calf ejection fraction, venous thrombosis, extent of reflux, pain, pigmentation, edema and ulceration. For example, direct venous pressure measurement may require the use of an invasive pressure transducer whilst non-invasive air plethysmography may make use of a mechanical cuff to determine blood volume changes and blood flow as a reflection of reflux, calf muscle pump and venous hypertension. It should be appreciated that photoplethysmography (PPG) differs from at least these existing measurements.

In various embodiments, the monitoring device 102 may be or may include a photoplethysmography (PPG) sensor.

In various embodiments, the PPG sensor may include a transducer configured to emit infrared light into a tissue site through a skin dermis of the subject, and a photodetector configured to receive the light reflected from the tissue site. The light reflected may be based on the number of red blood cells on the capillary bed. In other words, the PPG sensor may make use of the transducer that emits infrared light into the dermis; the amount of back-scattered light may depend on the number of red blood cells on the capillary bed, and may be measured by the photodetector, and displayed as a line tracing.

The flow and/or number of the red blood cells may provide an indication of the venous state of the subject.

The venous volume may refer to the volume of blood in the venous system or portion of the venous system. The venous volume of the leg may be determined when the plethysmographic curve reaches a maximum plateau. The change in the venous volume between before and after a particular activity performed by the subject, e.g. a tip-toe manoeuvre, may be referred to as an ejection volume. The ejection fraction (EF) is the ejection volume divided by the venous volume. The venous volume left after the particular activity may be referred to as a residual volume fraction. The residual volume divided by the venous volume may be termed as the residual volume fraction (RVF). The outflow fraction is the venous volume emptied per second.

The veins in the leg may be allowed to be refilled until the venous volume is again achieved. The venous volume may thus be referred to venous refill.

In various embodiments, the PPG sensor may act an indicator of venous pooling by measuring venous refill time (VRT). For example, the PPG sensor may be configured to measure a venous state after the subject ceases ambulation, wherein the venous state may include a venous refill time (VRT). Venous refill or recovery time (VRT) may be defined as the time required for the PPG tracing to return to about 90% of baseline. In other words, the VRT may be the time taken to reach about 90% of the venous volume or refill of the calf and may be used as an estimate of amount of venous pooling/stasis in the subject. The longer the VRT, the less the venous pooling.

The venous filling index (VFI) may be obtained by dividing 90% of the venous volume or refill by the time required to reach 90% of the venous volume or refill in an upright position.

The apparatus 100 in accordance with various embodiments may aim to use venous refill time measured using photoplethysmography (PPG) to provide an indication of venous pooling to inform stimulation parameters.

There may be no clinical need for the dynamic monitoring of the venous state as in-hospital/clinic assessment tools may be deemed sufficient for clinician assessment. Examples of such tools may include direct venous measurements, duplex ultrasound and less commonly, air plethysmography. However, these current assessment techniques are significantly bulky and may require a trained practitioner to administer. Due to the unique positioning of the PPG sensor around the ankle of the subject with its fast assessment time, the PPG sensor may be a choice tool for venous monitoring. The proposed monitoring tool may be from an inherent insight to the affected patient (subject) who may benefit from a dynamic assessment and effective treatment regime for his/her chronic condition.

By pairing the PPG sensor (the monitoring device 102) and the posterior tibial nerve stimulation (the NMES device 104) at the same location around the ankle of the subject or at least substantially near to the ankle of the subject, a wireless feedback communication may be possible as opposed to the use of lead wires in existing devices. However, it may also be envisioned the monitoring device 102 is electrically coupled to the NMES device 104 via one or more lead wires or electrical interconnections.

The apparatus 100 in accordance with various embodiments may further include an electromyography (EMG) sensor configured to measure muscle activation of the subject, wherein the NMES device 104 is further configured to adjust at least one of a frequency or an intensity of the electrical stimulus based on the measured muscle activation to effect supramaximal muscle contraction to the subject.

The apparatus 100 may further include at least one activity sensor configured to sense at least one of a physiological parameter, a postural parameter, an ambulatory parameter, and a gait parameter of the subject.

In various embodiments, the apparatus may include a processor. The processor may include an electrostimulation software.

The NMES device 104 may include a controller configured to interface with the processor or the electrostimulation software to provide the electrical stimulus dependent on the at least one of the physiological parameter, the postural parameter, the ambulatory parameter, and the gait parameter. In various embodiments, the controller may be configured to wirelessly interface with the electrostimulation software. In various embodiments, the processor or the electrostimulation software may interface with the at least one activity sensor via wired or wireless means. The processor may include a receiver or may be electrically coupled to a receiver to receive information related to the at least one of the physiological parameter, the postural parameter, the ambulatory parameter, and the gait parameter of the subject.

In various embodiments, the at least one activity sensor may include a breathing sensor, wherein the physiological parameter may include a respiratory parameter.

In other embodiments, the at least one activity sensor may include an accelerometer, wherein the postural parameter may include a sitting status or a standing status.

In yet other embodiments, the at least one activity sensor may include at least one of an accelerometer or a gyroscope, wherein the ambulatory parameter may include a stationary status or a walking status.

In yet other embodiments, the at least one activity sensor may include an accelerometer of gait, wherein the gait parameter may include a heel-strike status or a toe-strike status.

For example, the at least one activity sensor may be arranged to be placed at any one of the subject's chest, knee, right heel and left heel depending on the type of parameter to be sensed. In some instances, one activity sensor may be arranged to be placed at the subject's chest, knee, right heel and left heel.

The apparatus 100 may further include a disposable adhesive electrode strap or a patch to allow for easy placement of the apparatus 100 on a skin surface of the subject upon use, and/or for close approximation of the at least one electrode to the skin surface. For example, "close approximation" may mean in contact with, or at least substantially near to, or adjacent to. As non-limiting examples, the at least one electrode may be positioned within 3 mm, or within 2 mm, or within 1 mm from the skin surface.

The apparatus 100 may include a visual indicator configured to aid proper positioning of the apparatus 100 on a skin surface around an ankle of the subject or at least substantially near to an ankle of the subject.

The apparatus 100 may include a wearable cuff, or a sock.

The apparatus 100 may be or may include a portable, battery-operated apparatus. The apparatus 100 may include a compartment for receiving one or more batteries. The compartment may include one or more power electrodes for electrically coupling the one or more batteries to the other parts of the apparatus 100 such as the monitoring device 102 and/or the NMES device 104

The apparatus 100 in accordance with various embodiments may further include a battery indicator configured to indicate a level of battery power of the apparatus.

The apparatus 100 in accordance with various embodiments may further include a photoplethysmography (PPG) indicator configured to indicate the venous state of the subject. In various embodiments, the PPG indicator may be coupled to a PPG sensor, controllers and component that inform a user of a venous state of the subject. The subject may also be the user. The PPG indicator may be housed in a same unit as an electrical stimulation controller (i.e. the NMES device 104) or as an adjunct component that may be easily attached to the electrical stimulation controller.

In various embodiments the monitoring device 102 and the NMES device 104 may be housed in the same unit. The unit may also be referred to as a controller unit.

The apparatus 100 in accordance with various embodiments may further include a conductive medium for interposing between the at least one electrode and a skin surface of the subject. For example, the conductive medium may include a conductive gel.

The apparatus 100 in accordance with various embodiments may further include an automated timer configured to control a provision of the electrical stimulus at a predetermined time interval or based on at least one of the venous state determined by the monitoring device 102, a muscle activation measured by an electromyography (EMG) sensor, or at least one of the physiological parameter, the postural parameter, the ambulatory parameter, and the gait parameter sensed by the at least one activity sensor.

The apparatus 100 in accordance with various embodiments may further include a calibration unit configured to calibrate the NMES device 104 by adjusting the electrical stimulus to a level of maximal comfort and efficacy based on the subject's tolerance and sensitivity of the electrical stimulus.

The apparatus 100 in accordance with various embodiments may further include a processor configured to further process the electrical stimulus to eradicate components of the electrical stimulus that trigger sensitivity of sensory nerves located on a skin of the subject.

In various embodiments, the automated timer, the calibration unit and/or the processor may be housed in the controller unit.

In various embodiments, the apparatus 100 may be used with ambulation and is not limited to calf muscle inactivity only (e.g., as compared to some existing devices which typically perform assessments where a user (subject) is static or has calf muscle inactivity). In other words, the apparatus 100 in accordance with various embodiments may be used whether the subject is static or in motion and hence may not need to be paired with measurements of motion/ambulation/gait. For example, this may have special implications to CVI patients where they may suffer most from venous hypertension when they are ambulatory and hence the apparatus 100 that may be used whilst ambulatory would be most suitable.

Figure 2:
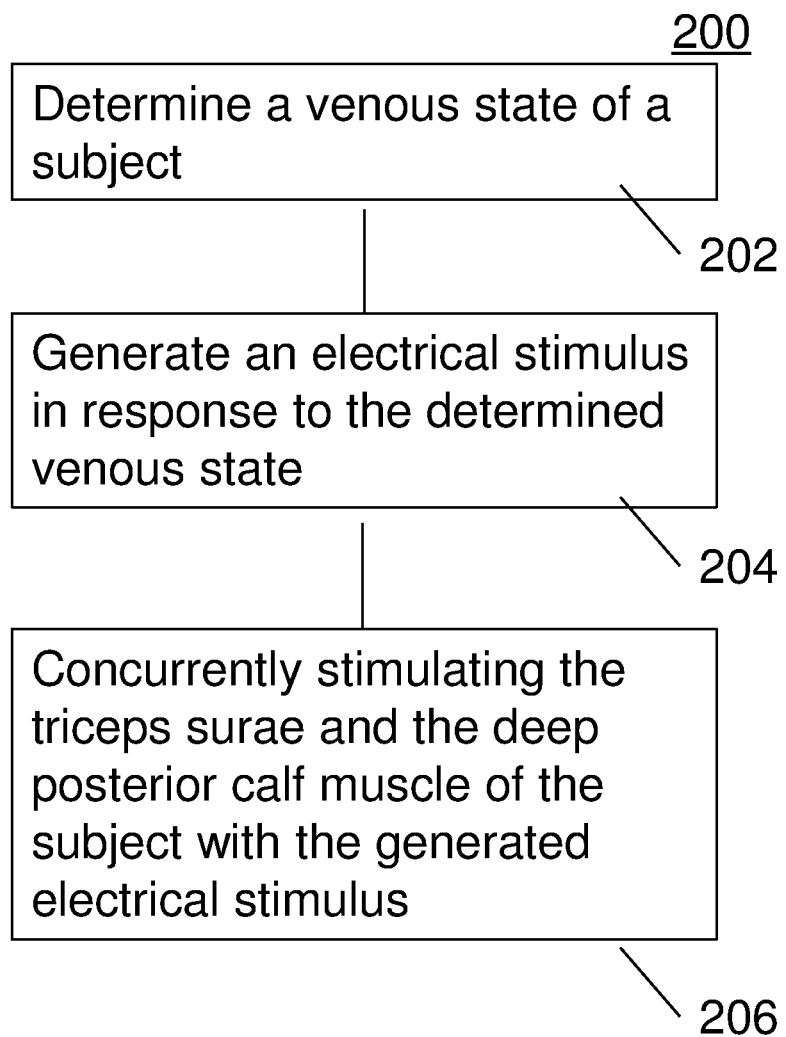
FIG. 2 is a schematic showing a method of enhancing lower limb venous return of a subject according to various embodiments.

FIG. 2 is a schematic 200 showing a method of enhancing lower limb venous return of a subject according to various embodiments. The method may include, in 202, determining a venous state of a subject. The method may also include, in 204, generating an electrical stimulus in response to the determined venous state. The method may further include, in 206, concurrently stimulating the triceps surae and the deep posterior calf muscle of the subject with the generated electrical stimulus.

In other words, the method may include determining a venous state of a venous system or blood circulatory system of a subject, providing an electrical stimulus based on the venous state determined. The electrical stimulus may stimulate both the triceps surae and the deep posterior calf muscle of the subject at the same time.

Monitoring the venous state may be carried out by the monitoring device as described herein. The electrical stimulus may be generated by the NMES device as described herein. The triceps surae and the deep posterior calf muscle may be stimulated by the at least one electrode as described herein.

The method may further include positioning a wearable non-invasive apparatus as described herein around an ankle of the subject or at least substantially near to an ankle of the subject.

In various embodiments, concurrently stimulating the triceps surae and the deep posterior calf muscle of the subject may cause the triceps surae and the deep posterior calf muscle to contract, thereby promoting the movement of venous blood.

In various embodiments, the generation of the electrical stimulus may be based on at least one of a physiological parameter, a postural parameter, an ambulatory parameter, and a gait parameter of the subject.

Figure 3:
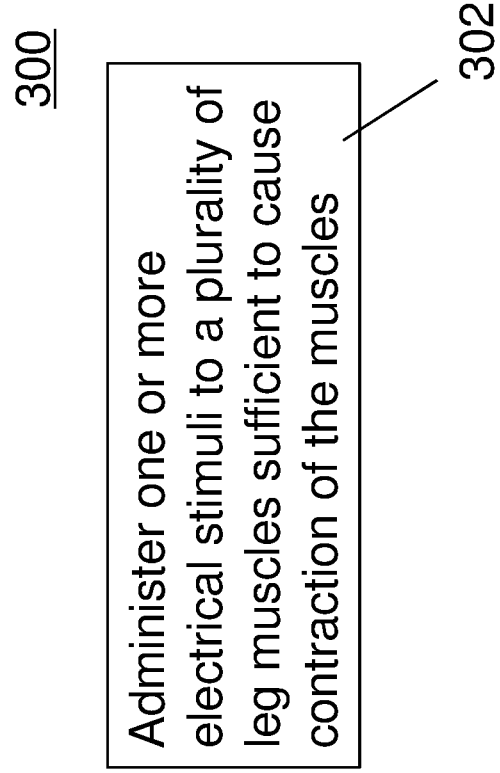
FIG. 3 is a schematic showing a method of treatment of a condition characterized by impaired blood flow in lower limbs according to various embodiments.

FIG. 3 is a schematic 300 showing a method of treatment of a condition characterized by impaired blood flow in lower limbs according to various embodiments. The method may include, in 302, administering one or more electrical stimuli to a plurality of leg muscles sufficient to cause contraction of the muscles. Preferably, the calf muscle and/or the ankle and/or the foot musculature may be stimulated. It may be preferred that the applied electrical stimulus may be efficacious in eliciting sufficient muscular contraction to promote movement of venous blood centrally towards the abdomen.

The plurality of leg muscles may be electrically stimulated at the same time.

FIG. 4 is a schematic 400 showing a method of accurately identifying skin based access to targeted calf muscles, deep posterior muscles, or a nerve that targets the calf muscles according to various embodiments. For example, the targeted calf muscles may include the triceps surae consisting of soleus and gastrocnemius, the deep posterior muscles may include posterior tibialis, flexor hallucislongus, flexor digitorumlongus and popliteus, and the nerve that targets the calf muscles may include the tibia vein and/or the posterior tibia vein. The method may include in 402, identifying the head of the fibula on the superiolateral aspect of the calf, in 404, extending a leg with the foot placed at maximal active or passive dorsiflexion, and in 406, identifying the soleus to run between the posterior edge of the fibula and the anteriolateral aspect of the gastrocnemius muscle along the superior third of the calf.

FIG. 5 is a schematic 500 showing a method of forming a wearable non-invasive apparatus for enhancing lower limb venous return of a subject according to various embodiments. The method may include, in 502, coupling a monitoring device to a neuromuscular electrical stimulation (NMES) device. The monitoring device may be configured to determine a venous state of a subject. The neuromuscular electrical stimulation (NMES) device may be configured to generate an electrical stimulus in response to the determined venous state and concurrently stimulate the triceps surae and the deep posterior calf muscle of the subject with the generated electrical stimulus to enhance lower limb venous return.

Figure 6A:
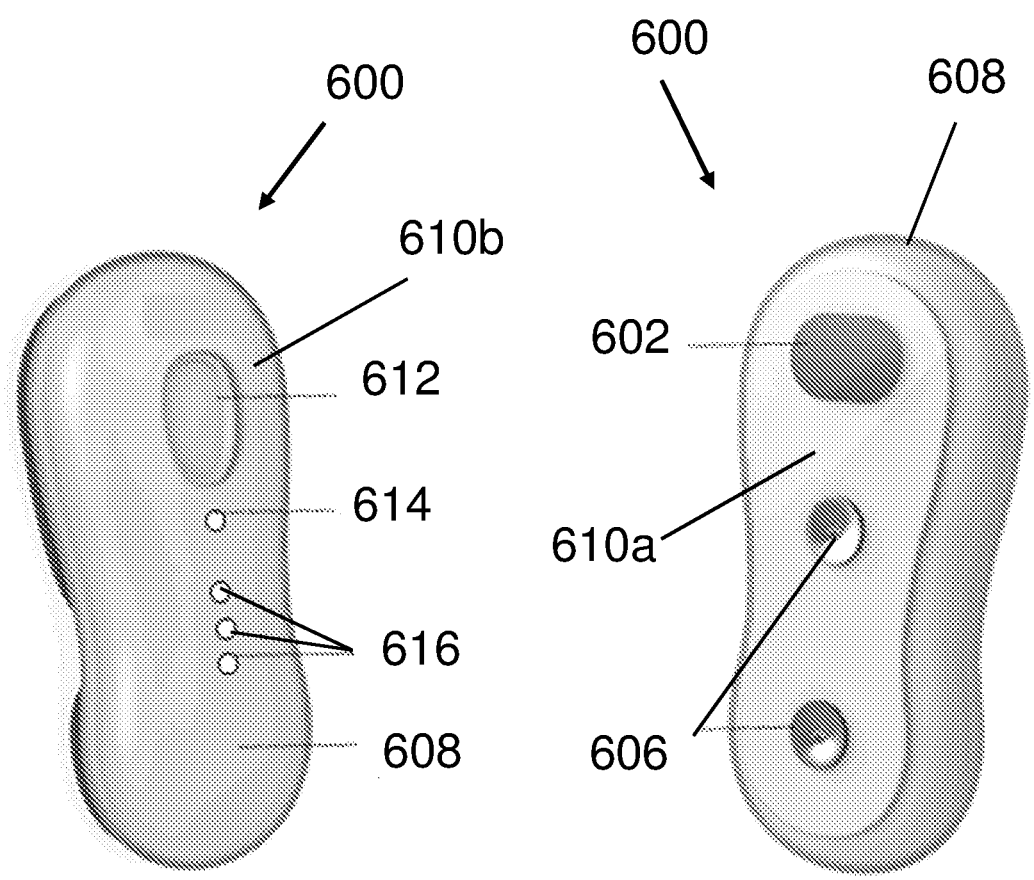
FIG. 6A shows the front and back exterior views of a controller unit of a wearable non-invasive apparatus according to various embodiments.
Figure 6B:
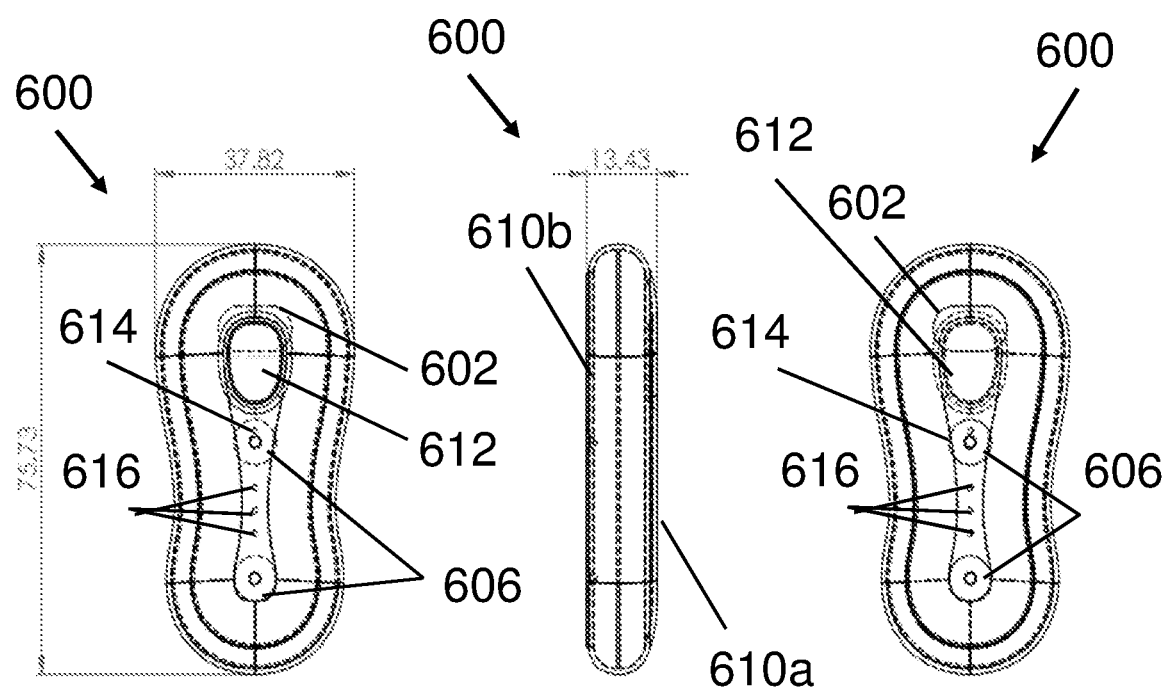
FIG. 6B shows the cross-sectional views of the controller unit according to various embodiments.

FIG. 6A shows the front and back exterior views of a controller unit 600 of a wearable non-invasive apparatus according to various embodiments. FIG. 6B shows the cross-sectional views of the controller unit 600 according to various embodiments. The controller unit 600 may include a monitoring device 602, e.g. a photoplethysmography (PPG) sensor, and a neuromuscular electrical stimulation (NMES) device which is not visible in FIG. 6A.

The schematic on the right shows the back view of the controller unit 600. The monitoring device 602 and the NMES device may be held by a housing 608 such as a soft over mold sleeve. During use, the back surface 610*a* of the controller unit 600 may face the skin or come into contact with the skin. The PPG sensor 602 may extend to the surface of the housing 608 so that the PPG sensor 602 faces the skin. In addition, the controller unit 600 may include one or more electrode contacts 606 on the back surface 610*a*. The one or more electrode contacts 606 may be electrically coupled the NMES device.

The schematic on the left shows the front view of the controller unit 600. The controller unit 600 may include a button 612, a status light-emitting diode (LED) 614, and intensity light-emitting diodes (LEDs) 616. The button 612 may be configured to turn on the controller unit 600 when depressed. When the button 612 is depressed while the controller unit 600 is on, the controller unit 600 may be switched off. The status LED 614 may indicate whether the controller unit 600 is switched on or switched off. The intensity LEDs 616 may indicate the intensity of the electrical stimulus generated by the NMES device.

Figure 6C:
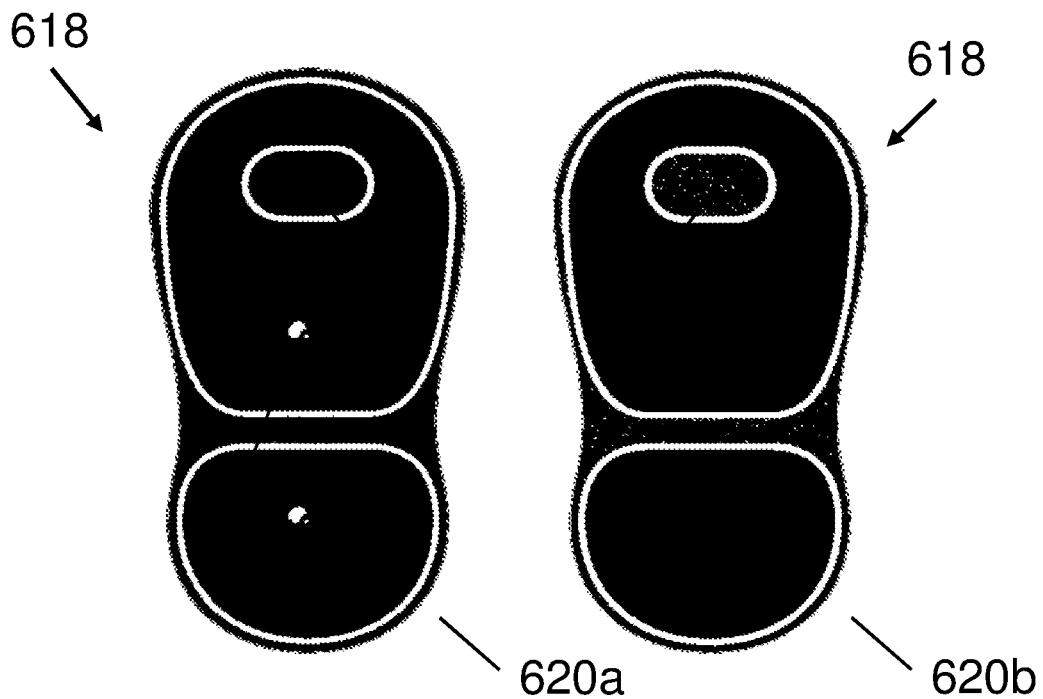
FIG. 6C shows the front (left) view and back view (right) of an electrode pad to be coupled to the controller unit according to various embodiments.
Figure 6D:
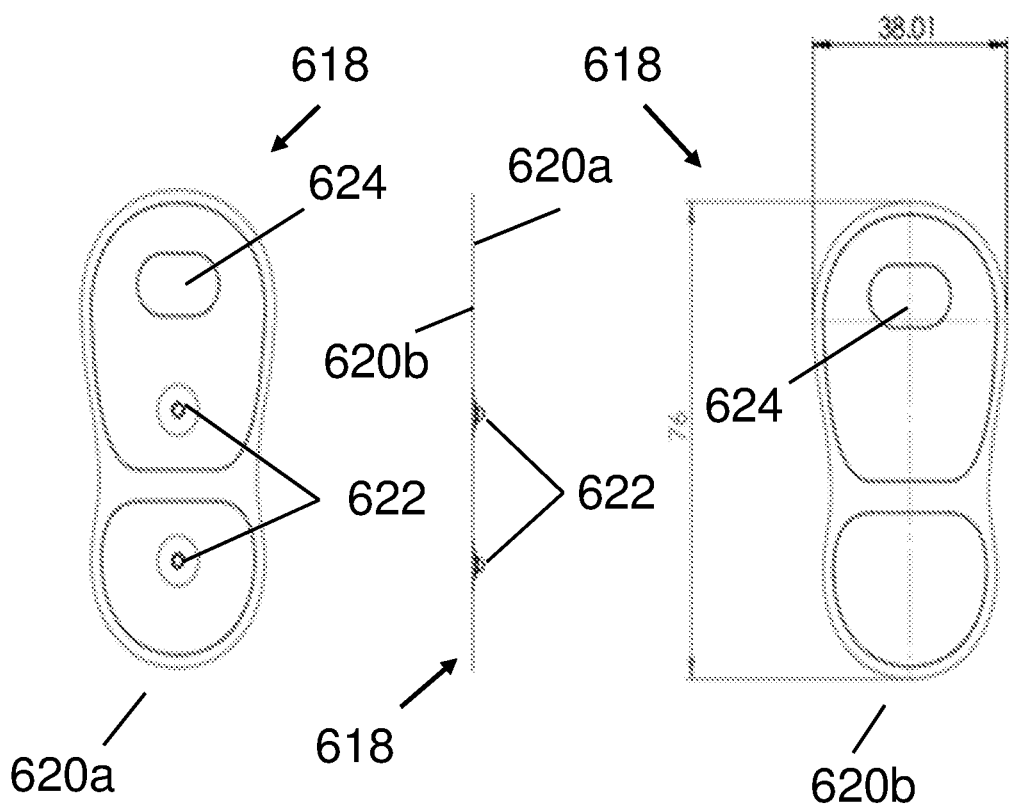
FIG. 6D shows the front view (left), side view (middle) and back view (right) of the electrode pad to be coupled to the controller unit according to various embodiments.

FIG. 6C shows the front (left) view and back view (right) of an electrode pad 618 to be coupled to the controller unit 600 according to various embodiments. FIG. 6D shows the front view (left), side view (middle) and back view (right) of the electrode pad 618 to be coupled to the controller unit 600 according to various embodiments. The electrode pad 618 may have a coupling side 620*a* for coupling to the controller unit 600*a* shown in FIGS. 6A and 6B. The electrode pad 618 may have one or more connectors 622 for coupling with the one or more electrode contacts 606 of the controller unit 600. The electrode pad 618 may further include a hole 624 so that when the electrode pad 618 is coupled to the controller unit 600 (through the one or more connectors 622 and the one or more electrode contacts 606), the PPG sensor 602 may pass through the hole 624 to be close to or be in contact with the skin. The electrode pad 618 may further include an exterior side 620*b* opposite the coupling side 620*a* for facing or contacting the skin.

Figure 6E:
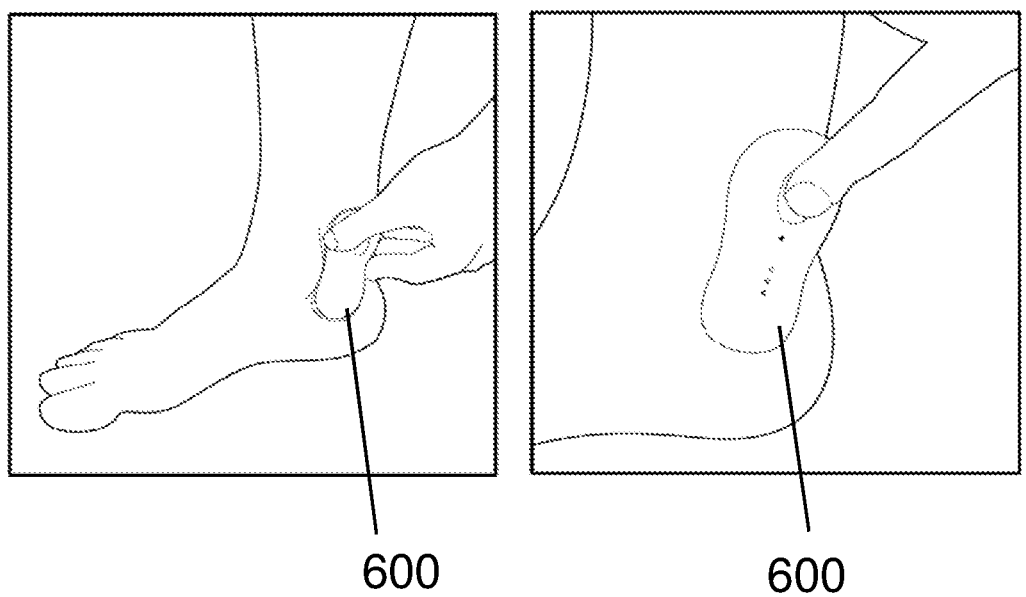
FIG. 6E shows the controller unit being attached to the skin at the ankle according to various embodiments.

FIG. 6E shows the controller unit 600 being attached to the skin at the ankle according to various embodiments. The electrode pad 618 (not shown in FIG. 6E) may be coupled to the controller unit 600 before use. The apparatus placed in the position shown may be ideal for directly targeting and effecting the tibial nerve.

The apparatus may be sleek and ergonomically designed, with dimensions of 6 cm (H)×3.5 cm (W)×1.5 cm (D).

The NMES device may concurrently stimulate the triceps surae and the deep posterior calf muscles to achieve a synergistic effect in increasing venous return in the lower limbs. Increasing venous return via stimulation may be possible by identifying the nerve, i.e. the tibial vein, that innervates all of these muscles. However, the tibial vein is deeply located at the popliteal fossa which requires a large amount of electrical current to effect stimulation. Various embodiments may seek to stimulate the targeted muscles via retrograde targeting through the posterior tibial nerve, a branch of the tibial nerve. However, various embodiments may additionally or alternatively target other nerves or other parts of the nerve that is upstream or downstream of the tibial nerve. Various embodiments may also directly target the muscles of interest.

Neuromuscular stimulation has been well studied and reported and utilized in many applications such as deep brain stimulation, transcutaneous electrical nerve stimulation and muscular stimulation. Various embodiments may make use of a range of electrical stimulus which has been assessed to be 1) tolerable to the user and/or 2) strong enough to stimulate the intended muscle contraction. The waveform administered may include a biphasic symmetrical or asymmetrical square wave pulse. The electrical stimulus applied may be at a current of between about 0 mA to about 100 mA, and may have a frequency of about 0.1 Hz to about 50 Hz. The electrical stimulus may be applied by a single electrode or a plurality of electrodes. The electrical stimulus may be an AC waveform or a DC waveform. The stimulus may be applied for a duration of between about 100 ms to about 750 ms, and may have a pulse width of between about 20 μs to about 1000 μs to produce the appropriate muscle contraction within the patient comfort zone. The electrical stimulus may be further processed to eradicate components of the waveform that trigger sensitivity of the sensory nerves located on the skin to increase comfort to the user.

Characteristics of the stimulus may vary over time. For example, a single stimulus may increase in current over the duration of the stimulus. Preferably, the increase may be gradual up to a peak. The stimulus may then either be maintained at the peak, terminate at the peak, or decrease in a gradual manner. Alternatively, where repeated stimuli are applied, characteristics of the stimuli may vary between different stimuli. For example, successive stimuli may be applied at increasing levels of current. Again, these successive stimuli may increase up to a peak gradually, followed by maintenance at that peak, or decrease from the peak. A cycle of increasing stimuli may be repeated a number of times. The optimized parameters may be used to preset various levels of intensity/frequency/pulse duration for optimum venous blood flow.

In various embodiments, the at least one electrode may be positioned at or near the posterior tibia nerve. The posterior tibial nerve is located along the posterior edge of the medial malleolus. The posterior tibial nerve runs within the tarsal tunnel as the most posterior structure; the other structures being the posterior tibial artery and vein, the flexor hallucis longus tendon, the flexor digitorum longus tendon, and the tibialis posterior tendon. The structures within the tarsal tunnel are secured in a semi rigid position against the medial malleolus by the flexor retinaculum, which attaches inferiorly to the calcaneus.

Placement of the at least one electrode may be performed by locating the medial malleolus and positioning the at least one electrode along its posterior edge. As the bony medial malleolus landmarks are prominent and permanent, positioning via the above method may generally be reliable. This location for stimulating the posterior tibial nerve may also be preferred due to the paucity of thick subcutaneous tissue in the area. A non-invasive method for electrically stimulating the posterior tibial nerve may be employed according to various embodiments.

In various embodiments, the at least one electrode may be positioned at or near various muscles. The gastrocnemius muscle includes the medial and lateral head. The medial head originates on the posterior surface of the femur superior to the medial condyle and posterior to the insertion of the adductor magnus muscle. The lateral head originates in the lateral epicondyle of the femur. Both insert into a long common muscle aponeurosis which forms the Achilles tendon with the aponeurosis of the soleus. The proximal part of the muscle forms the lower triangle of the popliteal fossa. The muscle bellies extend from the popliteal fossa to the mid to distal third of the leg. The medial and lateral head run side by side and are separated by a fibrous septum.

The position on the gastrocnemius muscle where at least one electrode may be placed may be determined by palpating the superior edge where the two muscle bellies meet, or palpating the most inferior point of the popliteal fossa. The at least one electrode may also be placed along the inferior midline before the two muscle bellies diverge. This point may be ideally palpated with the foot in maximal dorsiflexion.

The soleus is a large flat muscle that attaches superiorly to the head of the fibula and along the posterior and medial aspects of the tibia. Its muscle fibers extend inferiorly along the posterior aspect of the lower leg to form the achilles tendon (along with the gastrocnemius muscle fibers). The achilles tendon subsequently attaches to the heel bone. The soleus may be non-invasively accessed via the superior third of the posterior calf, in between the medial and lateral heads of the gastrocnemius, although it may also be accessed via the inferiolateral aspect of the posterior calf. It may also be preferably accessed via the superiolateral aspect of the calf. The location of the soleus may be determined by the longitudinal position of the fibula, in particular, the head of the fibula, with reference to the gastrocnemius muscle.

The method may include identifying the head of the fibula on the superiolateral aspect of the calf. The method may also include extending the leg with the foot placed at maximal active or passive dorsiflexion. The soleus may be identified to run between the posterior edge of the fibula and the anteriolateral aspect of the gastrocnemius muscle along the superior third of the calf.

Figure 7A:
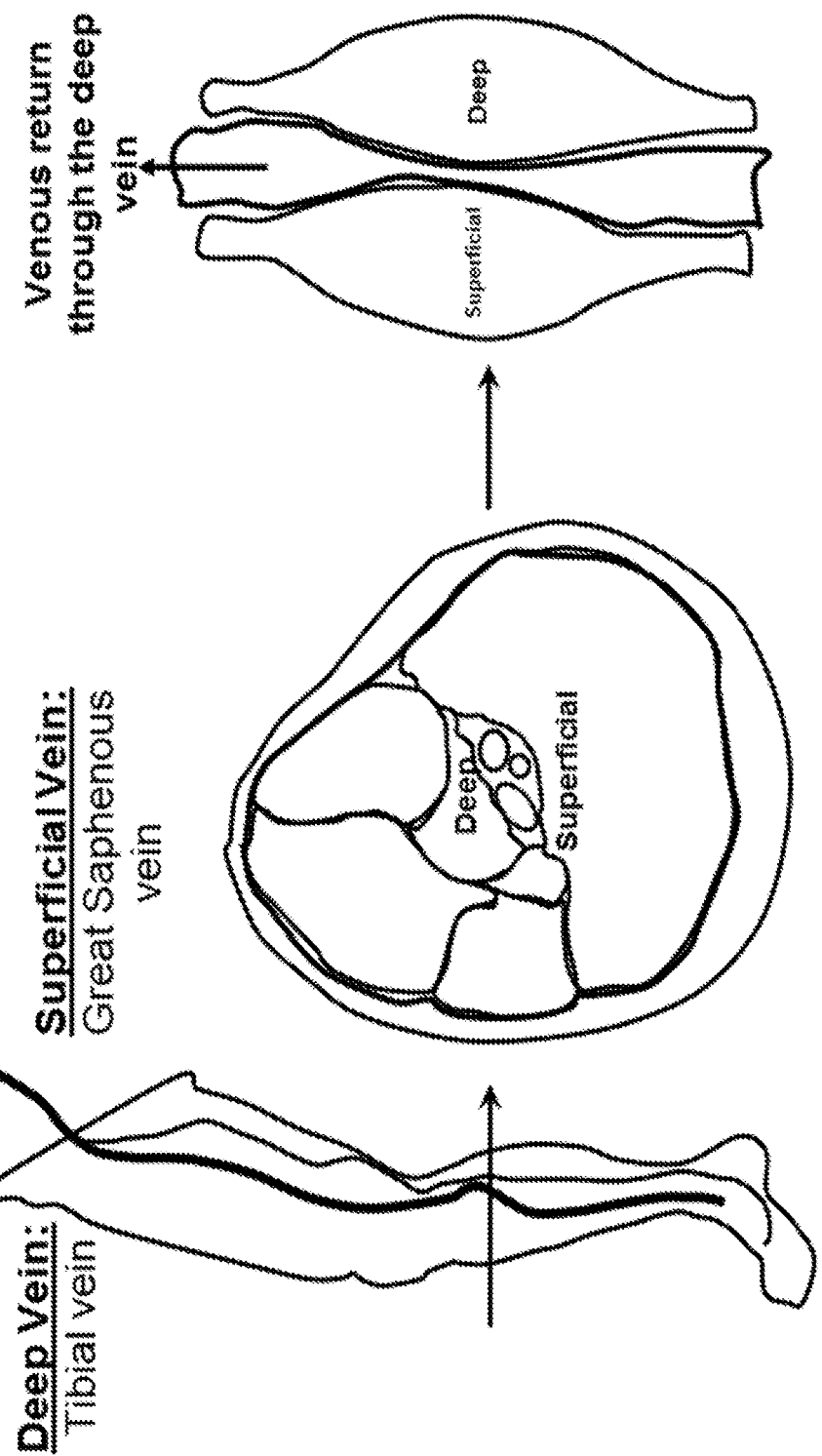
FIG. 7A is a schematic showing using superficial and deep muscles to synergistically enhance venous return via calf muscle pump according to various embodiments.
Figure 7B:
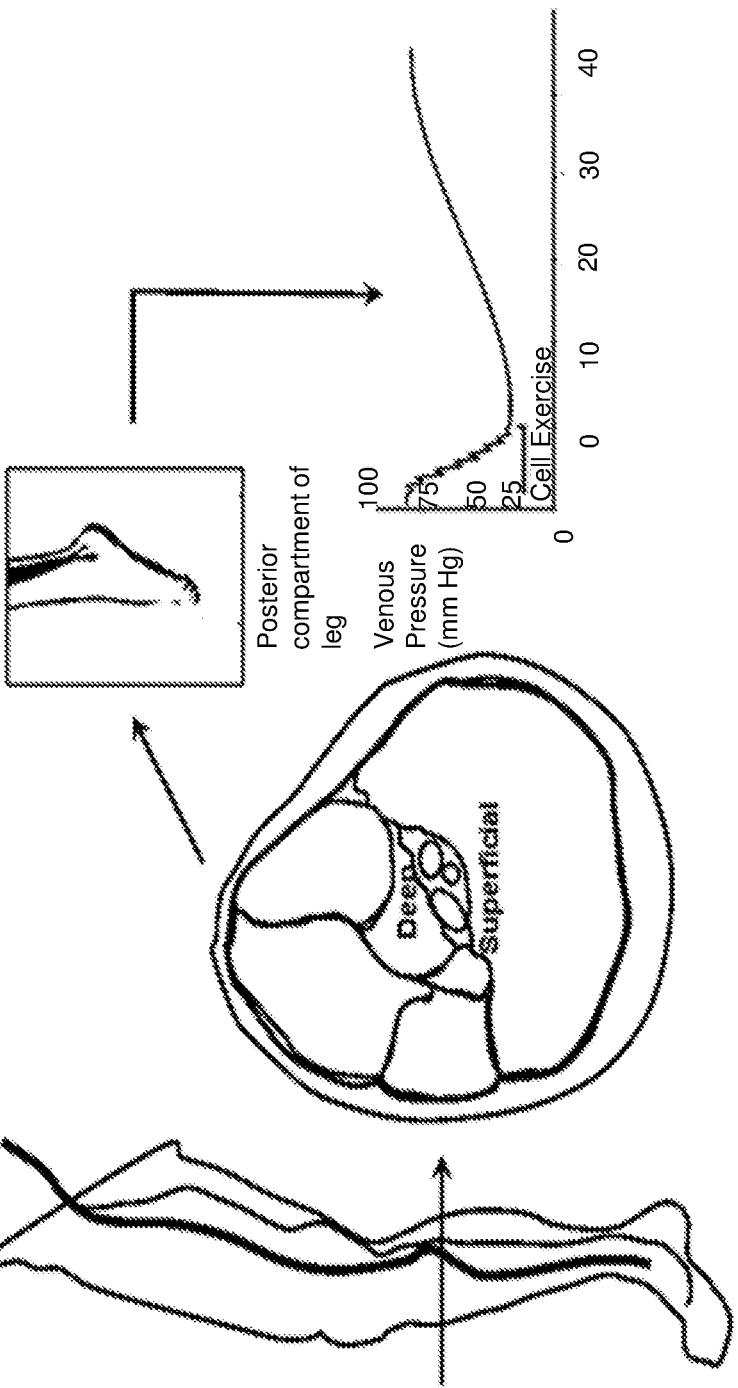
FIG. 7B is a schematic showing using superficial and deep muscles to synergistically enhance venous return via the venous foot pump by encouraging plantar flexion according to various embodiments.

FIG. 7A is a schematic 700a showing using superficial and deep muscles to synergistically enhance venous return via calf muscle pump according to various embodiments. FIG. 7B is a schematic 700b showing using superficial and deep muscles to synergistically enhance venous return via the venous foot pump by encouraging plantar flexion according to various embodiments. FIG. 7C is a schematic 700c showing the targeting of the posterior tibial nerve to stimulate superficial and deep muscles via peripheral and central pathways according to various embodiments.

Various embodiments may provide a method of treatment of a condition characterized by impaired blood flow in lower limbs. The method may include administering one or more electrical stimuli to a plurality of leg muscles sufficient to cause contraction of the muscles. Preferably the calf muscle and/or the ankle and/or the foot musculature may be stimulated. It may be preferred that the applied electrical stimulus is efficacious in eliciting sufficient muscular contraction to promote movement of venous blood centrally towards the abdomen, and that the stimuli are painless and non-irritating to the user. Based on the workings of Pascal's law whereby external pressure applied to a closed system is transmitted equally in all directions within the contained area which is currently the basis for compression treatment in CVI patients, various embodiments may seek to draw parallels by possibly simultaneously stimulating muscles of the deep posterior compartment of the lower leg to provide an equal and resistive external internal 'compression' pressure along the length of the deep posterior tibia vein. These muscles include but are not limited to the soleus and the posterior tibialis (TP), the flexor digitorum longus (FDL), the flexor hallucis longus (FHL), and the popliteus.

The TP is located on the superior aspect of the posterior surface of tibia and from the intermuscular septum between muscles of posterior compartment and deep transverse septum. Inversion of the foot against resistance allows for identification of the TP muscle along the posterior groove of the tibia above the medial malleolus.

The FDL and FHL muscles are located deep within the deep posterior compartment, at the posterior surface of the fibula and the tibia respectively. A small gap of access to the FDL muscle along the lateral side of the tibia at the junction between the upper ⅓ and middle-third of the lower limb may serve as an access point for stimulation of the deep posterior calf muscles.

The stimulation of deep posterior calf muscles may serve two purposes: 1) to provide a synergistic effect to existing triceps surae stimulation to enhance return via the calf muscle pump, and 2) to enhance stimulation of plantar flexion to stimulate venous return via the foot pump.

The NMES settings may be customized to the user through an initial baseline assessment of 1) user tolerance i.e. via sensory nerve conductance and/or 2) ability to effect supramaximal muscle contraction via the placement of electromyography (EMG) sensors. The NMES settings may be re-calibrated after a pre-determined period of use, for example, weeks-months, to promote incremental performance of venous return at least until a physiological acceptable range of venous return, for example, abolishment of lower limb venous reflux (>0.5 s) as determined by duplex ultrasound or via other means of clinical assessment.

The venous state may be defined using the following variables: outflow fraction, venous filling index, venous refill time, ejection volume, ejection fraction, venous volume, and residual volume fraction. Additional parameters of venous state measurement besides plethysmography may include, but are not limited to, skin turgor, edema or tissue oxygen perfusion, pain, inflammation, and induration. The NMES settings may be further customized to the user through the use of a non-invasive sensor of venous refill time using photoplethysmography (PPG), which is a non-invasive tool used to provide an overall functional assessment of the venous system. The wearable PPG sensor may be incorporated into the electropad and may be positioned above the medial malleolus and used as a form of monitoring to provide incremental performance of venous return via NMES, as well as an assessment tool to indicate severity of CVI, which may be made known to the user or the patient.

The PPG sensor may include a transducer that emits infrared light into the skin dermis. The infrared light may be back-scattered by the skin dermis. The amount of back-scattered light may depend on the number of red blood cells on the capillary bed, and may be measured by a photodetector. The measurement may be done at the end of an electrical stimulation session. The electrical stimulation session may cause the user to plantar flex his/her foot which partially empties the venous reservoir in the calf and skin, which is then registered as a change in the infrared absorption of the skin. Alternatively, the PPG reading may be programmed to measure venous refill or recovery time (VRT) after patient ceases ambulation. The venous refill time or recovery time (VRT) may be defined as the time required for the PPG tracing to return to 90% of baseline after cessation of exercise, and may be shorter in a limb with venous reflux. The venous refill time may refer to the time it takes blood to refill the microcirculation after a series of calf muscle contractions and emptying of the veins. A refill time ≥20 seconds may suggest normal venous filling. A rapid refill time <20 seconds may indicate an abnormal situation in which the calf pump is ineffective in ejecting blood with the engorged larger vessels quickly refill the smaller vessels.

Various embodiments may use the PPG sensor as a means for providing feedback to tailor subsequent stimulation frequency and duration in response to changes in the venous refill time. The addition of a PPG sensor to determine venous refill time may provide an indication of the venous health. Different stimulations with different frequency settings may then be delivered based on the indication of the venous health. For example, electrical stimulation may be carried out 5 times a day if VRT is less than 15 s, 3 times a day if VRT is less than 20 s, 1 time a day if VRT is more than 20 s. The stimulation may be carried out automatically based on the indication of the venous health, which obviates the need for constant monitoring by the user once the device is worn while still achieving efficacy.

Figure 7E:
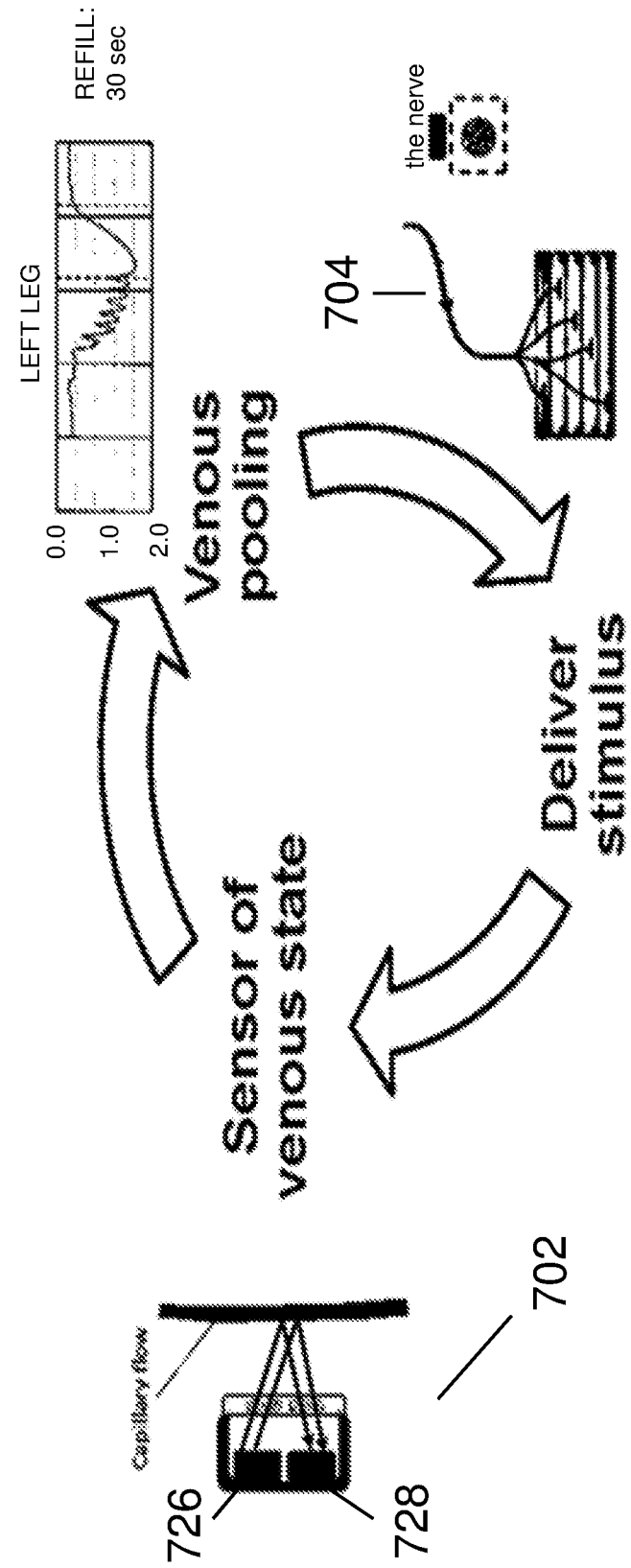
FIG. 7E is a schematic showing a continuous monitoring-feedback loop that allows for the titration of the stimulation dose based on the venous status of the user according to various embodiments.

FIG. 7D is a schematic 700d illustrating the use of a monitoring device according to various embodiments including a photoplethysmography (PPG) sensor 702 as an indicator of venous pooling. As highlighted above, the PPG sensor 702 may include a transducer 726 configured to emit infrared light into the dermis. The amount of back-scattered light may depend on the number of red blood cells on the capillary bed, and may be measured by a photodetector 728 and displayed as a line tracing. The VRT may be used as an indicator of venous pooling. The longer the VRT, the less the venous pooling. The electrical stimulus may be generated by the NMES device 704 based on the venous pooling. FIG. 7E is a schematic 700e showing a continuous monitoring-feedback loop that allows for the titration of the stimulation dose based on the venous status of the user according to various embodiments.

The monitoring device may include the PPG sensor 702, one or more controllers, and one or more components that would inform the user of their venous state. The monitoring device may be housed in the same unit as the NMES device 704 (which may also be referred to as an electrical stimulation controller) or as an adjunct component that could be easily attached to the NMES device 704. Additionally or alternatively, the venous state may also be assessed through skin turgor, edema, tissue oxygen perfusion, and/or venous hypertension/pressure. The electrical stimulus may be generated by the NMES device 704 based on the venous status.

In various embodiments, the apparatus may be configured to provide a program of a single basic mode of pre-set low frequency, low intensity electrical stimulation (NMES) in increasing levels for all postural positions and ambulatory positions of the user that can be matched to the user's day-to-day physiological muscular function through calibration before use with fixed or set durations of use.

The apparatus may also be configured to provide an advanced program including three different modes of NMES made available to the CVI user for which venous reflux due to gravitational forces is known to occur, namely, sitting, standing and walking/running. These modes may be additionally coupled with the sensing of knee-to-thoracic height, respiration and gait respectively. These modes may be initiated or switched based on readings from three-dimensional xyz accelerometer wired or wireless sensors placed at four locations: chest, knee, right heel and left heel. A baseline measurement/calibration may be made upon fitting. The vertical heights of the sensors may be determined. For instance, the vertical height of the chest sensor may be denoted as $ychest_1$, the vertical height of the knee sensor may be denoted as $yknee_2$, while the vertical heights of the right heel sensor and the left heel sensor may be denoted as $yrightheel_3$ and $ylefthe el_4$ respectively. Subsequently, when turned on, the smart sensors may transmit real-time information to either an attached or a remote receiver/controller which interfaces with the electrostimulation software (wired/or wireless) to determine the according NMES output.

Aside from gravitational forces, when a person is sitting, there may be an increased intra-abdominal pressure exerted which is likely coupled with the entrapment of blood in the femoral vein in the sitting position. The bent knee position may also result in a possible entrapment (complete/incomplete) of blood in the popliteal vein. In various embodiments, the apparatus may be configured to determine that the person or the user is in a 'sitting' mode. The sitting position may be identified or determined from the chest sensor ($ychest_1$) and knee sensor ($yknee_2$) as a decrease in a difference between the vertical heights of the sensors ($ychest_1-yknee_{2sitting}<ychest_1-yknee_{2standing}$) perpendicular to the ground. The value of $ychest_1-yknee_{2standing}$ may be known from the baseline measurement/calibrations. When the chest sensor and knee sensor detects that the relative heights between each other is lower that the baseline measurements, the chest sensor and the knee sensor may determine that the user is sitting.

Various embodiments may alternatively do away with sensors for determining whether the user is in a sitting position or a standing position or is walking/running. The user may manually change between a 'standing' mode, a 'walking/running' mode (or 'ambulatory' mode), and a 'sitting' mode on the apparatus or the device. The NMES delivered when the user is sitting may be of an increased frequency and intensity as compared to the 'standing' mode/ 'walking' mode as the calf muscles may not be engaged in the 'sitting' mode. The soleus is the most effective muscle for plantar flexion in a bent knee position. The NMES may be adjusted by applying an electrical stimulus to the soleus such that the user is able to achieve slight plantar flexion. Simultaneous stimulation of the TP, FHL and FDL muscles at electrical muscle stimulation (EMS) parameters sufficient to promote adequate contraction as observed by slight inversion of the foot may also be applied. Simultaneous stimulation of the above-mentioned muscles may help with the venous return of the lower limb in a sitting position.

When a person is standing upright, there may an 'uninterrupted' venous return column from the feet to the heart, i.e. without entrapment of blood at the popliteal and femoral vein junctions. Nevertheless, distinct pressure segmentations may occur throughout the venous return column, which may be due to the interplay of 1) intra-thoracic pressure, 2) intra-abdominal pressure, and 3) presence of a series of valves in veins. Altogether, these may result in alternating pressure differential segments that drive venous return and prevent venous reflux. By coupling respiration patterns to the delivery or electrical stimulation, synergistic lower limb venous return may be achieved.

For example, the pressure in the abdominal cavity of a recumbent person may normally average about +6 mmHg During inspiration, the intrathoracic pressure may be negative (suction of air into the lungs), and the abdominal pressure may be positive (compression of abdominal organs by diaphragm). When the intra-abdominal pressure rises, the pressure in the veins of the legs may need to rise above the abdominal pressure before the abdominal veins open and allow the blood to flow from the legs to the heart. During pregnancy or obesity, this intra-abdominal pressure may rise to about +15 to about +30 mmHg, which are high risk factors for CVI. If a person stands perfectly still, the venous pump does not work, and the venous pressure in the lower legs may increase to the full gravitational value of 90 mm Hg in about 30 seconds. The pressure in the capillaries may also increase greatly, causing fluid to leak from the circulatory system into the tissue spaces. As a result, the legs may swell, and the blood volume may diminish.

Figure 7F:
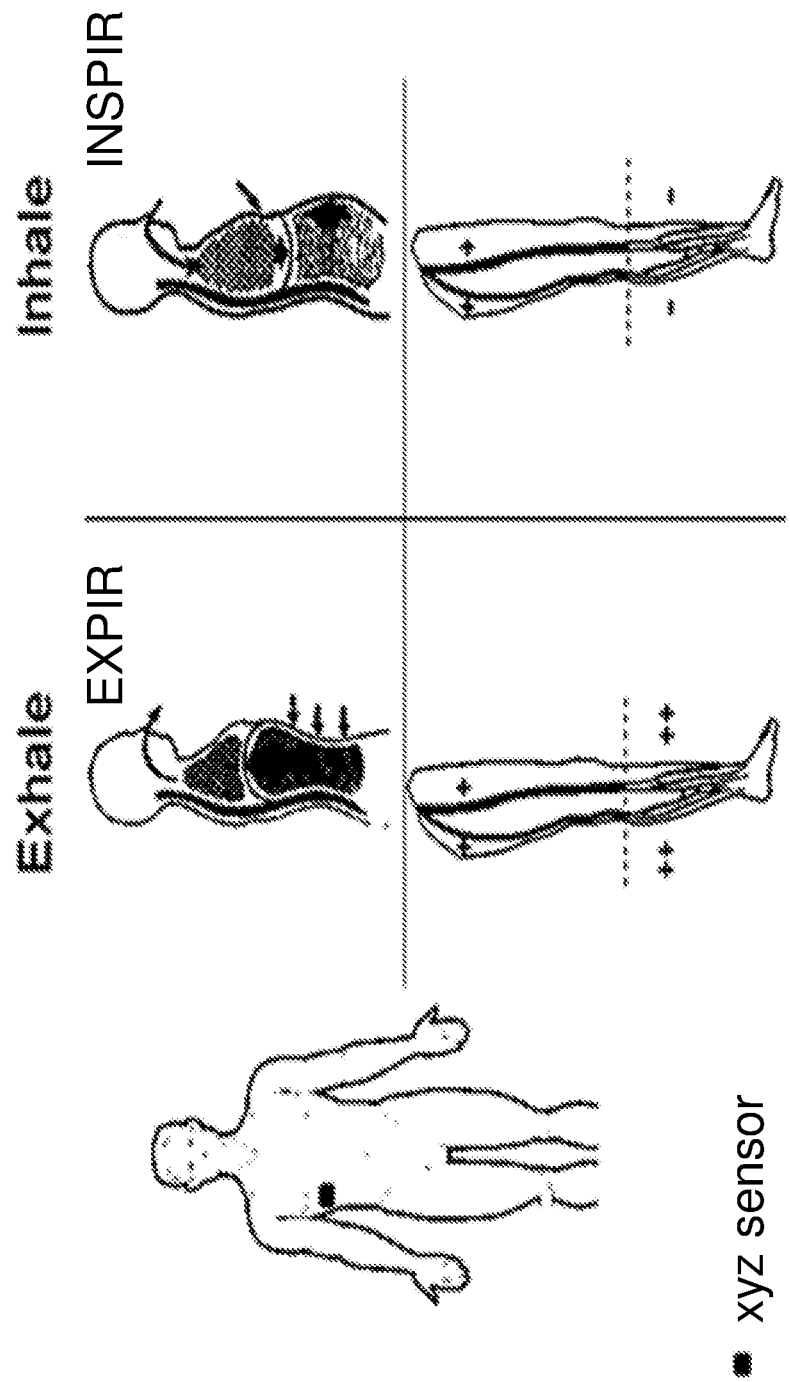
FIG. 7F is a schematic showing how an accelerometer sensor configured to determine movements in three dimensions (xyz sensor) is used with a neuromuscular electrical stimulation (NMES) device for electrical stimulation based on breathing (exhalation/inhalation) according to various embodiments.

To enhance lower limb venous return in the standing position, firstly, the chest sensor, the knee sensor and the heel sensors may need to determine that the user is in a standing position (i.e. $ychest_1 - yknee_{2standing}$ value are equal to baseline measurements/calibration values, while the heel sensors may not record any motion). Next, the accelerometer sensor on the chest may record the relative x-axis positions of the sensor, i.e. inspiration $(x_{inp})$–expiration $(x_{exp})$, during rib-cage expansion. FIG. 7F is a schematic 700f showing how an accelerometer sensor configured to determine movements in three dimensions (xyz sensor) is used with a neuromuscular electrical stimulation (NMES) device for electrical stimulation based on breathing (exhalation/inhalation) according to various embodiments. If intra-abdominal pressure is deemed a major contribution to the lower limb venous return, NMES may be applied to the soleus, the posterior tibialis (TP), the flexor digitorum longus (FDL), and/or the flexor hallucis longus (FHL) during which the intra-abdominal pressure during physiological standing is the lowest at the point of maximum exhalation $x_{exp}$, i.e. when the rib cage circumference is the smallest. The stimulation may be applied for the duration that is equivalent to the period of exhalation (time duration when the x-position of the chest sensor is between a maximum value $x_{inpmax}$ and a minimum value $x_{expmin}$).

Alternatively, if the intra-thoracic pressure is deemed to be a significant contribution of respiration that stimulates venous return from the lower limb circulatory, NMES may be applied in the reverse from the above, when intra-thoracic pressure is most negative upon inhalation i.e. $x_{inpmax}$. The electrical stimulation may be applied for the duration that is equivalent to the period of exhalation (time duration when the x-position of the chest sensor is between a minimum value $x_{expmin}$ and a maximum value $x_{inpmax}$).

Various embodiments may be suitable for application of electrical stimulus when the user is walking. The apparatus may be configured not to inhibit ambulation and not to cause instability. The apparatus may also be configured to enhance venous return based on the gait of the user. In various embodiments, electrical stimulation may be applied in coordination with locomotor activity either via gait, cardiac—locomotor synchronization and/or pressure distribution along the foot.

For example, for gait sensing, the apparatus or device may be configured to determine if the user is in an upright position, i.e. $ychest_1 - yknee_{2standing}$ values are equal to baseline measurements/calibration values.

The sensors on the heels may record or detect the rising of the heel as the foot lifts off when walking. The sensors on the heels may be further configured to determine a heel-strike or a toe-strike. When the right foot is in contact with the ground, $yrightheel_3=0$. Similarly, when the left foot is in contact with the ground $ylefteel_4=0$. The apparatus may be attached to the right foot. When $yrightheel_3=0$, the NMES may be turned on in preparation for contracting the patient's existing deep calf muscle. When the right heel rises above the ground in preparation for foot lift off, i.e. $yrightheel_3>0$, the NMES signal may be turned off to allow for a period of rest. The application of the electrical stimulus when the foot is in contact with the ground may enhance the potential or benefit of the electrical stimulus.

Altogether, the timing of electrical stimulation of the deep calf muscles in accordance with walking gait may synergistically enhance the physiological function of the calf muscle pump to stimulate lower limb venous return. Alternatively, pressure sensors placed on the ball of the soles of the feet may be used as a NMES switch to turn off the electrical stimulation to the calf muscles just before the foot goes into a toe-off position. For pressure sensing, the application of a pressure sensor that can sense a weight of up to 45 kg equivalent or more on the ball of the feet may be used to activate NMES.

The apparatus or device may also include accelerometers and/or gyroscopes which are inertial sensors to detect motion with respect to an inertial coordinate system. The input from these sensors may be processed to generate a current indicating whether the subject/apparatus is at rest or in motion. Noise due to random stops during ambulation e.g. stopping for a traffic crossing, to answer a phone call, may be filtered out and conversely, noise due to movement at rest e.g. vibration, ankle movement may also be filtered out. The information gathered may be used to improve the safety of electrical stimulation, which may pose a risk to people, for instance elderly patients, by causing instability whilst they are walking and increasing the risk of falls. For example, electrical stimulation of the tibial nerve may only be effected when the user is detected to be stationary after a set period of time, and the NMES device may be programmed to turn off when the patient stands up and prepares to move.

In various embodiments, the apparatus or device may be in the form of a wearable cuff, an adhesive patch or a sock. The controller unit may be attached to at least one electrode via snap buttons. The at least one electrode may be attached to the skin via a combination of adhesive and hydrogel.

Alternatively, the at least one electrode may be conventional electrodes, for example, reusable types such as those used in transcutaneous electric nerve stimulation (TENS) applications, or disposable electrodes of the type commonly used for electrocardiogram (ECG) applications. The electrodes may be self-adhering, repositionable, semi-adhering, and/or may include a conductive gel for ensuring skin contact. Alternatively, the apparatus may include a conductive gel, and/or may include an alternative conductive medium for interposing between the electrode and the skin of the user. For example, the apparatus or the device may include a liner impregnated with a conductive gel or an electrolyte between the electrode and the user. The liner may be conductive in restricted locations, for example, at a number of specific locations over the liner, which may allow stimuli to be applied at a number of locations on a limb of the user using only a single electrode. Various embodiments may be tailored for daily wear, and may be configured to be worn during ambulation. The controller unit may be small, portable, with simple to use pre-attached lead wires or remote/wireless control, and pre-loaded batteries or rechargeable batteries.

Figure 8A:
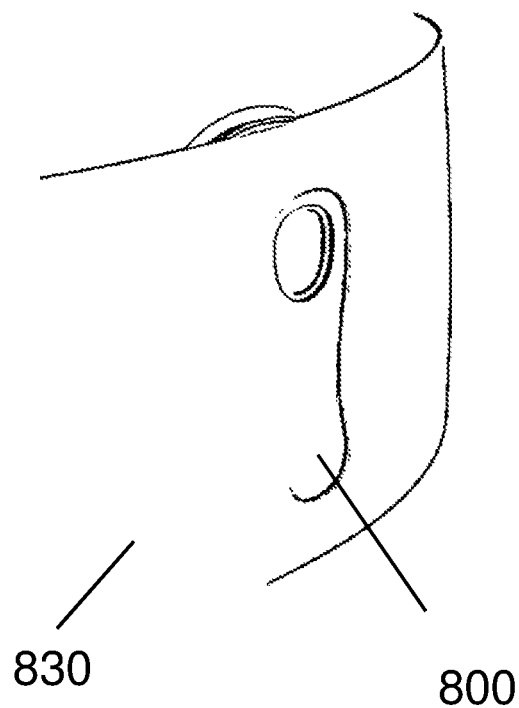
FIG. 8A shows a front view of a neoprene Velcro strap for holding a controller unit in place during active use according to various embodiments.
Figure 8B:
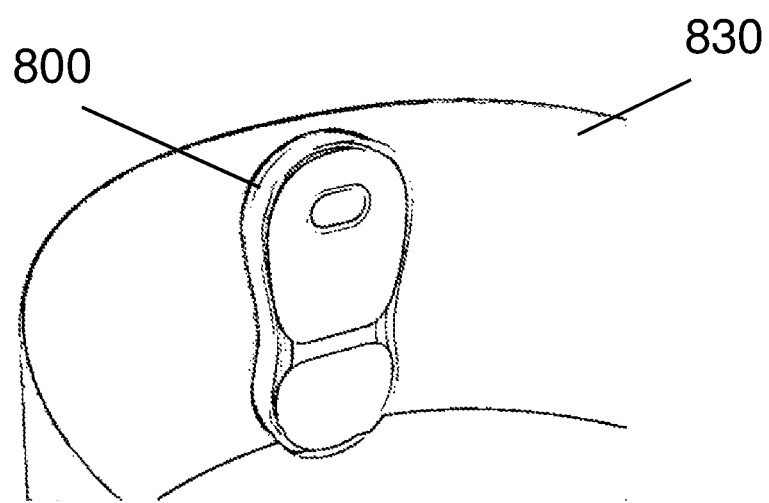
FIG. 8B shows a back view of the neoprene Velcro strap for holding the controller unit in place during active use according to various embodiments.

FIG. 8A shows a front view of a neoprene Velcro strap 830 for holding a controller unit 800 in place during active use according to various embodiments. FIG. 8B shows a back view of the neoprene Velcro strap 830 for holding the controller unit 800 in place during active use according to various embodiments.

Preliminary studies have been carried out which demonstrate (1) a positive trend in the synergistic stimulation of the deep posterior muscles in addition to the triceps surae with an increase venous return volume at the popliteal vein; and (2) a significant venous return when a tolerable electrical stimulus is applied to the posterior tibial nerve.

Figure 9A:
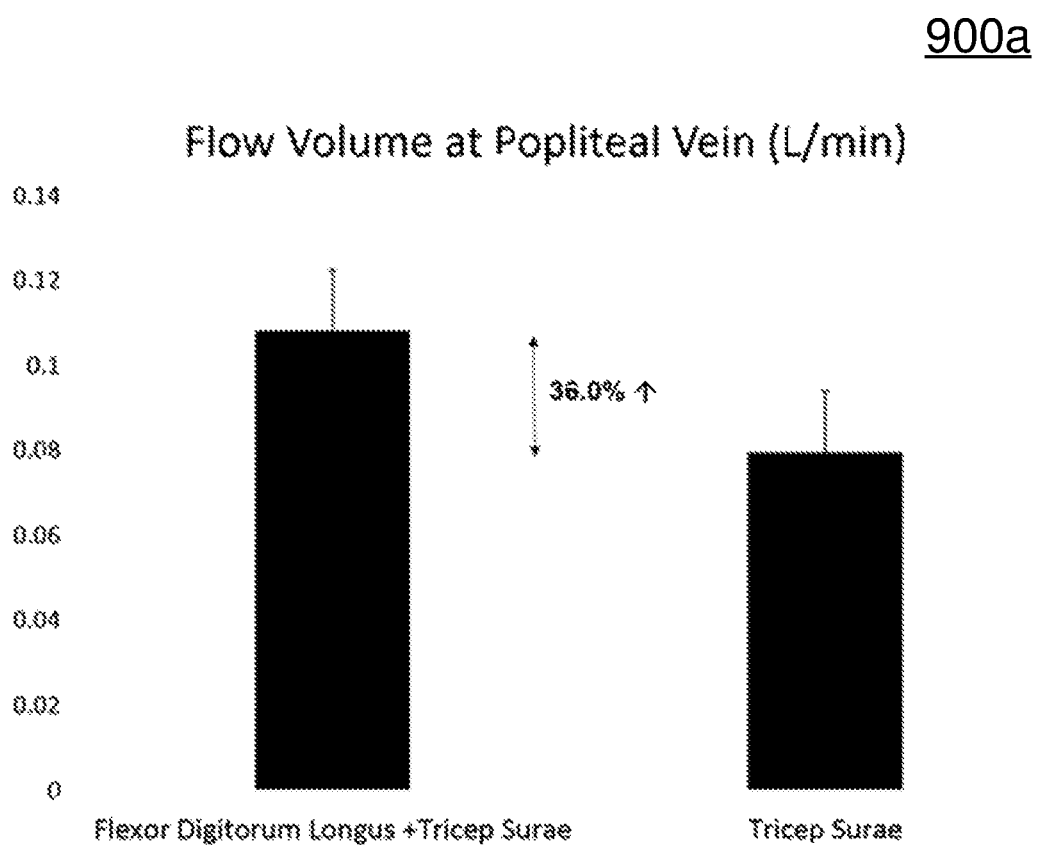
FIG. 9A is a bar diagram showing the flow volume (litres per minute or L/min) along the popliteal vein when electrical stimulation is applied to both the flexor digitorum longus muscle and the tricep surae muscle according to various embodiments and when electrical stimulation is applied only to the tricep surae muscle.

FIG. 9A is a bar diagram 900a showing the flow volume (litres per minute or L/min) along the popliteal vein when electrical stimulation is applied to both the flexor digitorum longus muscle and the tricep surae muscle according to various embodiments and when electrical stimulation is applied only to the tricep surae muscle. The simultaneous stimulation of the triceps surae and the deep posterior calf muscles i.e. flexor digitorum longus shows a higher flow rate along the popliteal vein as compared to stimulation of the triceps surae alone.

Figure 9B:
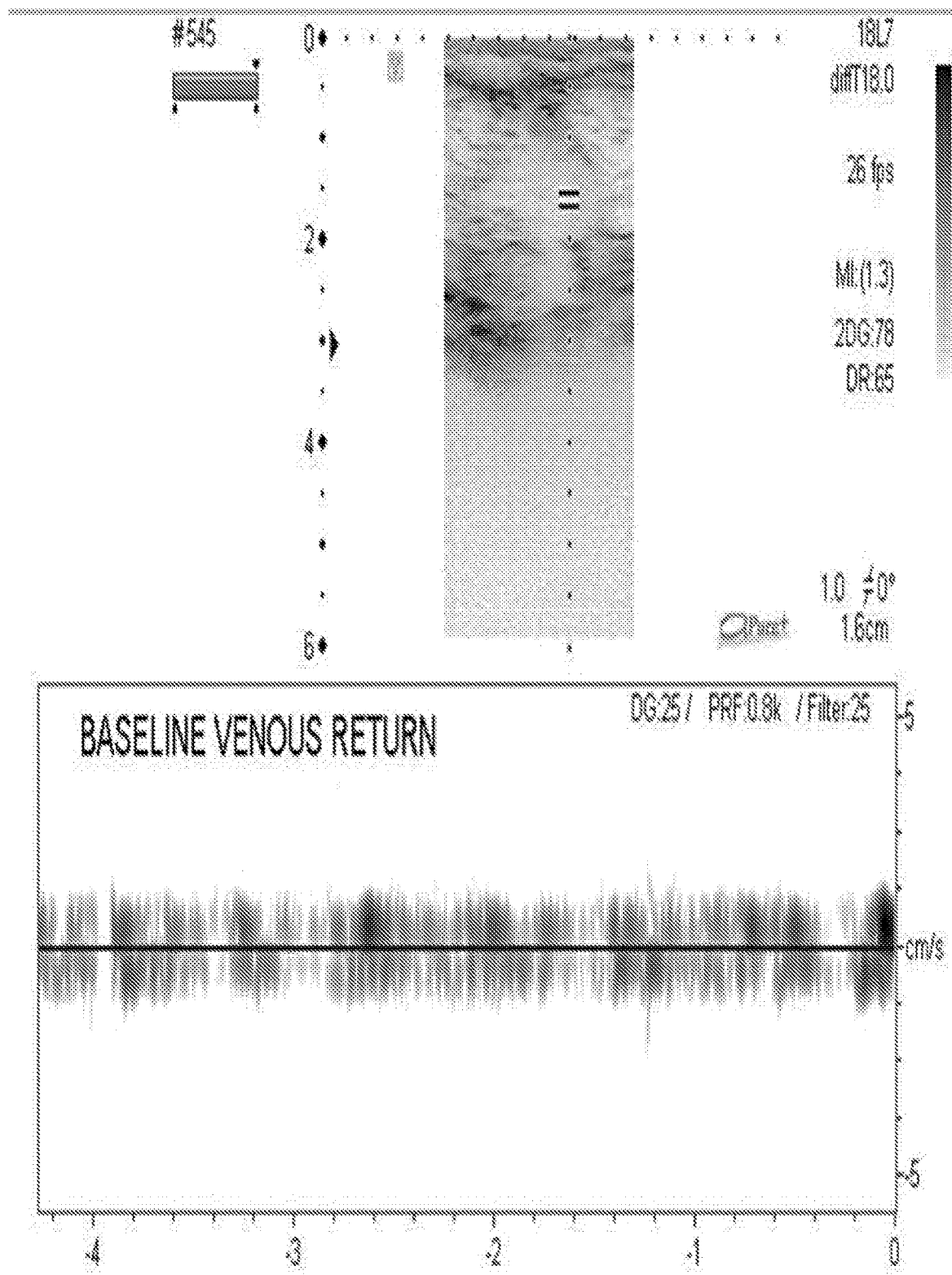
FIG. 9B shows a graph of baseline mean peak venous velocity (centimetre per second or cm/s) as a function of time (seconds or s) according to various embodiments.
Figure 9C:
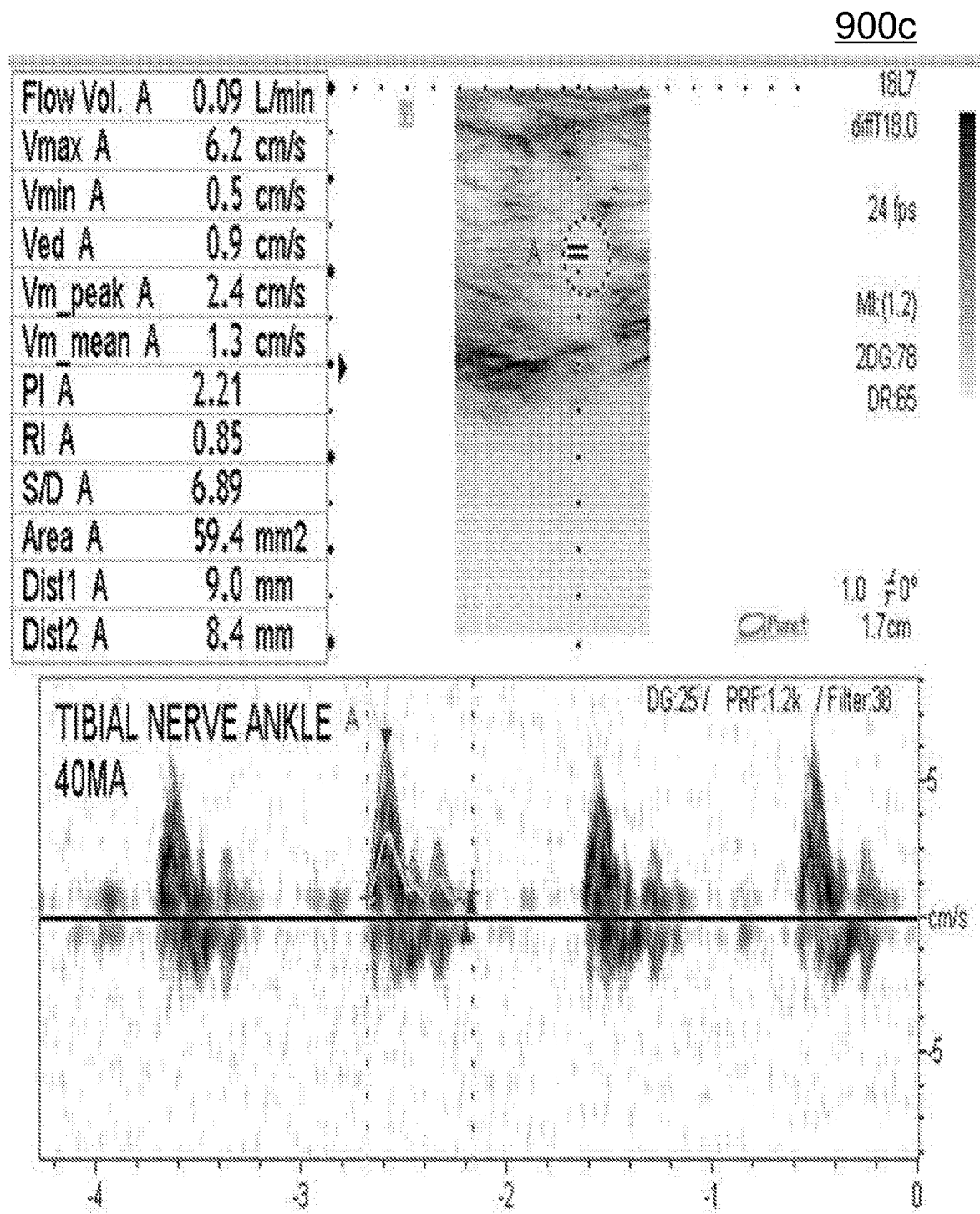
FIG. 9C shows a graph of mean peak venous velocity (centimetre per second or cm/s) as a function of time (seconds or s) during stimulation of the posterior tibial nerve according to various embodiments.

FIG. 9B shows a graph 900b of baseline mean peak venous velocity (centimetre per second or cm/s) as a function of time (seconds or s) according to various embodiments. FIG. 9C shows a graph 900c of mean peak venous velocity (centimetre per second or cm/s) as a function of time (seconds or s) during stimulation of the posterior tibial nerve according to various embodiments. FIGS. 9B and 9C show that stimulation of the posterior tibial nerve provides a significant increase in mean peak venous velocity and flow volume at the popliteal vein compared to baseline resting venous return.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A wearable non-invasive apparatus for enhancing lower limb venous return of a subject, the apparatus comprising:
   a controller unit comprising:
      a monitoring device comprising a photoplethysmography sensor configured to determine a venous state indicated by a flow of red blood cells in a subject; and
      a neuromuscular electrical stimulation (NMES) device configured to generate an electrical stimulus in response to the determined venous state and further configured to concurrently stimulate a triceps surae and a deep posterior calf muscle of the subject with the generated electrical stimulus to enhance lower limb venous return; and
   an electrode pad coupled to the controller unit and configured to be placed in contact with a skin surface around an ankle of the subject;
   wherein the electrode pad comprises a hole so that the photoplethysmography sensor passes through the hole when the electrode pad is coupled to the controller unit.

2. The apparatus of claim 1, wherein the electrode pad is adapted to be positioned at the triceps surae of the subject, or the deep posterior calf muscle of the subject, or a tibial nerve of the subject to retrograde target the triceps surae and the deep posterior calf muscle of the subject.

3. The apparatus of claim 2, wherein the electrode pad is adapted to be positioned at the triceps surae selected from the group consisting of the gastrocnemius muscle and the soleus muscles.

4. The apparatus of claim 2, wherein the electrode pad is adapted to be positioned at the deep posterior calf muscle selected from the group consisting of a flexor digitorum longus muscle, flexor hallucis longus, posterior tibialis and popliteus muscles.

5. The apparatus of claim 2, wherein the at least one electrode is adapted to be positioned at the tibial nerve through a posterior tibial nerve.

6. The apparatus of claim 1, wherein the NMES device is configured to provide retrograde neurostimulation of a posterior tibial nerve of the subject.

7. The apparatus of claim 1, further comprising at least one activity sensor configured to sense at least one of a physiological parameter, a postural parameter, an ambulatory parameter, and a gait parameter of the subject.

8. The apparatus of claim 7, wherein the NMES device comprises a controller configured to interface with an electrostimulation software to provide the electrical stimulus dependent on the at least one of the physiological parameter, the postural parameter, the ambulatory parameter, and the gait parameter.

9. The apparatus of claim 8, wherein the controller is configured to wirelessly interface with the electrostimulation software.

10. The apparatus of claim 1, further comprising a disposable adhesive electrode strap or a patch to allow for easy placement of the apparatus on a skin surface of the subject upon use.

11. The apparatus of claim 1, further comprising an visual indicator configured to aid proper positioning of the apparatus on a skin surface around an ankle of the subject or at least substantially near to an ankle of the subject.

12. The apparatus of claim 1, further comprising a wearable cuff, or a sock.

13. The apparatus of claim 1, wherein the apparatus comprises a portable, battery-operated apparatus.

14. A method of enhancing lower limb venous return of a subject, the method comprising:
   determining a venous state of a subject using a photoplethysmography sensor of a monitoring device of a controller unit, the venous state indicated by a flow of red blood cells; and
   generating an electrical stimulus in response to the determined venous state using a neuromuscular electric stimulation (NMES) device of the controller unit; and
   concurrently stimulating a triceps surae and a deep posterior calf muscle of the subject with the generated electrical stimulus using the neuromuscular electrical stimulation (NMES) device;
   wherein the controller unit is coupled to an electrode pad, the electrode pad configured to be placed in contact with a skin surface around an ankle of the subject; and
   wherein the electrode pad comprises a hole so that the photoplethysmography sensor passes through the hole when the electrode pad is coupled to the controller unit.

15. The method of claim 14, further comprising positioning a wearable non-invasive apparatus, the wearable non-invasive apparatus comprising the controller unit and the electrode pad, around an ankle of the subject or at least substantially near to an ankle of the subject.

* * * * *